(12) United States Patent
Corbett

(10) Patent No.: US 6,881,844 B2
(45) Date of Patent: Apr. 19, 2005

(54) INDOLE-3-CARBOXAMIDES AS GLUCOKINASE ACTIVATORS

(75) Inventor: Wendy Lea Corbett, Randolph, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 10/674,481

(22) Filed: Sep. 30, 2003

(65) Prior Publication Data
US 2004/0067939 A1 Apr. 8, 2004

Related U.S. Application Data

(60) Provisional application No. 60/415,737, filed on Oct. 3, 2002.

(51) Int. Cl.$^7$ ............................................. C07D 209/02
(52) U.S. Cl. .................. 546/201; 548/139; 548/492
(58) Field of Search ................. 548/492, 139; 546/201

(56) References Cited

U.S. PATENT DOCUMENTS

| | | |
|---|---|---|
| 6,262,096 B1 | 7/2001 | Kim et al. |
| 6,433,188 B1 | 8/2002 | Corbett et al. |
| 6,441,184 B1 | 8/2002 | Corbett et al. |
| 6,448,399 B1 | 9/2002 | Corbett et al. |
| 6,482,951 B1 | 11/2002 | Guertin |
| 6,545,155 B1 | 4/2003 | Corbett et al. |

FOREIGN PATENT DOCUMENTS

| | | |
|---|---|---|
| EP | 1346982 | 9/2003 |
| JP | 01/139550 | 5/2001 |
| WO | WO 97/17064 | 5/1997 |
| WO | WO 99/24416 | 5/1999 |
| WO | WO 02 53534 | 7/2002 |
| WO | WO 03 106462 | 12/2003 |

OTHER PUBLICATIONS

Khalaf et al., Synthesis of novel DNA binding agents: indole containing analogs of bis–netropsin, 2000, Science Reviews Ltd., 6, pp. 264–265.*

* cited by examiner

Primary Examiner—Taofiq Solola
Assistant Examiner—Robin Waller
(74) Attorney, Agent, or Firm—George W. Johnston; Dennis P. Tramaloni; Eileen M. Ebel

(57) ABSTRACT

The present invention provides glucokinase activators of formula I:

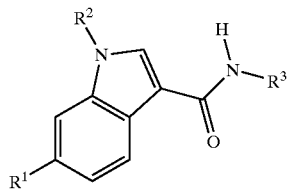

wherein $R^1$, $R^2$ and $R^3$ are defined in the specification. Glucokinase activators are useful for increasing insulin secretion in the treatment of type II diabetes.

20 Claims, No Drawings

INDOLE-3-CARBOXAMIDES AS GLUCOKINASE ACTIVATORS

PRIORITY TO RELATED APPLICATIONS

This application claims the benefit of Provisional Application Ser. No. 60/415,737, filed Oct. 3, 2002.

BACKGROUND OF THE INVENTION

Glucokinase (GK) is one of four hexokinases that are found in mammals [Colowick, S. P., in *The Enzymes*, Vol. 9 (P. Boyer, ed.) Academic Press, New York, N.Y., pages 1–48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97–115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10–15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463–496, 1993]. These findings contributed over a decade ago to the hypothesis that GK functions as a glucose sensor in β-cells and hepatocytes (Meglasson, M. D. and Matschinsky, F. M. *Amer. J. Physiol.* 246, E1–E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69–78, 1995; Ferrie, T., Riu, E., Bosch, F. et al., *FASEB J.*, 10, 1213–1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167–173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226–230, 1998). While mutations of the GK gene are not found in the majority of patients with type II diabetes, compounds that activate GK, and thereby increase the sensitivity of the GK sensor system, will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

The present invention provides a compound of formula I:

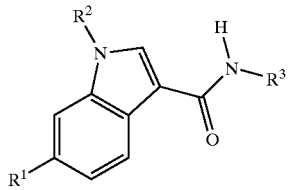

I wherein $R^1$ is halo, nitro, amino, cyano, methyl, trifluoromethyl, hydroxy, methoxy, trifluoromethoxy, methylthio, methylsulfinyl, or methylsulfonyl;

$R^1$ is lower alkyl having from 2 to 5 carbon atoms or —$CH_2$—$R^4$ wherein $R^4$ is cycloalkyl having from 3 to 6 carbon atoms; and $R^3$ is an unsubstituted or mono-substituted five- or six-membered heteroaromatic ring connected by a ring carbon atom to the amine group shown, which five- or six-membered heteroaromatic ring contains from 1 to 3 heteroatoms selected from sulfur, oxygen or nitrogen, with one heteroatom being nitrogen which is adjacent to the connecting ring carbon atom; said mono-substituted heteroaromatic ring being mono-substituted at a position on a ring carbon atom other than adjacent to said connecting carbon atom with a substituent selected from the group consisting of methyl, trifluoromethyl, chloro, bromo, nitro, cyano,

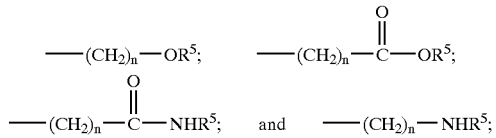

wherein n is 0 or 1;

$R^5$ is hydrogen or lower alkyl;

or a pharmaceutically acceptable salt thereof.

The compounds of formula I have been found to activate glucokinase in vitro. Glucokinase activators are useful for increasing insulin secretion in the treatment of type II diabetes.

DETAILED DESCRIPTION OF THE INVENTION

The present invention provides compounds, which are amides in accordance with formula I:

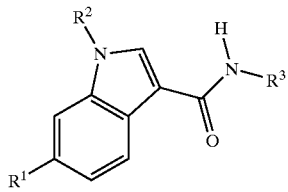

I wherein $R^1$ is halo, nitro, amino, cyano, methyl, trifluoromethyl, hydroxy, methoxy, trifluoromethoxy, methylthio, methylsulfinyl, or methylsulfonyl;

$R^2$ is lower alkyl having from 2 to 5 carbon atoms or a —$CH_2$—$R^4$ wherein $R^4$ is cycloalkyl having from 3 to 6 carbon atoms; and R³ is an unsubstituted or mono-substituted five- or six-membered heteroaromatic ring connected by a ring carbon atom to the amine group shown, which five- or six-membered heteroaromatic ring contains from 1 to 3 heteroatoms selected from sulfur, oxygen or nitrogen, with one heteroatom being nitrogen which is adjacent to the connecting ring carbon atom; said mono-substituted heteroaromatic ring being mono-substituted at a position on a ring carbon atom other than adjacent to said connecting carbon atom with a substituent selected from the group consisting of methyl, trifluoromethyl, chloro, bromo, nitro, cyano,

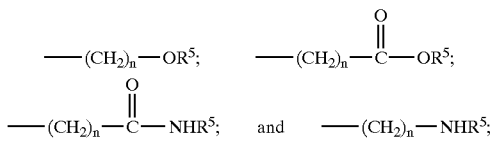

wherein n is 0 or 1;

R⁵ is hydrogen or lower alkyl;

or a pharmaceutically acceptable salt thereof.

As used throughout, the term "lower alkyl" includes both straight chain and branched chain alkyl groups having from 1 to 7 carbon atoms, such as methyl, ethyl, propyl, isopropyl, etc. Preferable lower alkyls are lower alkyls having from 2 to 5 carbon atoms such as propyl and isopropyl.

As used herein, "perfluoro-lower alkyl" means any lower alkyl group wherein all of the hydrogens of the lower alkyl group are substituted or replaced by fluoro. Among the preferred perfluoro-lower alkyl groups are trifluoromethyl, pentafluoroethyl, heptafluoropropyl, etc.

As used herein, "cycloalkyl" means a saturated hydrocarbon ring having from 3 to 10 carbon atoms. Preferred cycloalkyls have from 3 to 6 carbon atoms. A preferred cycloalkyl is cyclobutyl.

As used herein, each of the terms "halogen" and "halo", unless otherwise stated, designates all four halogens, i.e. fluorine, chlorine, bromine, and iodine. A preferred halogen is chlorine.

As used herein, the term "aryl" signifies aryl mononuclear aromatic hydrocarbon groups such as, for example, phenyl and tolyl, which can be unsubstituted or substituted in one or more positions with halogen, nitro, lower alkyl, or lower alkoxy. The term "aryl" also signifies polynuclear aryl groups such as, for example, naphthyl, anthryl, and phenanthryl, which can be unsubstituted or substituted in one or more positions with halogen, nitro, lower alkyl, or lower alkoxy. Preferred aryl groups are the substituted and unsubstituted mononuclear aryl groups, particularly phenyl and tolyl. The term "arylalkyl" denotes an alkyl group, preferably lower alkyl, in which one of the hydrogen atoms can be replaced by an aryl group. Examples of arylalkyl groups are benzyl, 2-phenylethyl, 3-phenylpropyl, 4-chlorobenzyl, 4-methoxybenzyl and the like.

As used herein, the term "lower alkoxy" includes both straight chain and branched chain alkoxy groups having from 1 to 7 carbon atoms, such as methoxy, ethoxy, propoxy, isopropoxy, preferably methoxy and ethoxy.

As used herein, the term "lower alkanoic acid" denotes lower alkanoic acids containing from 2 to 7 carbon atoms such as propionic acid, acetic acid and the like. The term "lower alkanoyl" denotes monovalent alkanoyl groups having from 2 to 7 carbon atoms such as propionoyl, acetyl and the like. The term "aroic acids" denotes aryl alkanoic acids where aryl is as defined above and alkanoic contains from 1 to 6 carbon atoms. The term "aroyl" denotes aroic acids wherein aryl is as defined hereinbefore, with the hydroxy group of the —COOH moiety removed. Among the preferred aroyl groups is benzoyl.

As used herein, "lower alkyl thio" means a lower alkyl group as defined above bound to a thio group that is attached to the rest of the molecule, e.g., methylthio. As used herein, "lower alkyl sulfinyl" means a lower alkyl group as defined above bound to a sulfinyl group (sulfoxide) that is attached to the rest of the molecule, e.g. methylsulfinyl. As used herein, "lower alkyl sulfonyl" means a lower alkyl group as defined above bound to a sulfonyl group that is attached to the rest of the molecule, e.g., methylsulfonyl.

During the course of synthetic reactions, the various functional groups such as the free carboxylic acid or hydroxy groups may be protected via conventional hydrolyzable ester or ether protecting groups. As used herein, the term "hydrolyzable ester or ether protecting groups" designates any ester or ether conventionally used for protecting carboxylic acids or alcohols which can be hydrolyzed to yield the respective carboxy or hydroxy group. Exemplary ester groups useful for those purposes are those in which the acyl moieties are derived from a lower alkanoic, aryl lower alkanoic, or lower alkane dicarboxylic acid. Among the activated acids which can be utilized to form such groups are acid anhydrides, acid halides, preferably acid chlorides or acid bromides derived from aryl or lower alkanoic acids. Examples of anhydrides are anhydrides derived from monocarboxylic acids such as acetic anhydride, benzoic acid anhydride, and lower alkane dicarboxylic acid anhydrides, e.g., succinic anhydride as well as chloro formates e.g., trichloromethyl chloroformate and ethyl chloroformate being preferred. A suitable ether protecting group for alcohols may be, for example, a tetrahydropyranyl ether such as 4-methoxy-5,6-dihydroxy-2H-pyranyl ethers. Other suitable ethers are aroylmethylethers such as benzyl, benzhydryl or trityl ethers or α-lower alkoxy lower alkyl ethers, for example, methoxymethyl or allylic ethers or alkyl silylethers such as trimethylsilylether.

The term "amino protecting group" designates any conventional amino protecting group which can be cleaved to yield the free amino group. The preferred protecting groups are the conventional amino protecting groups utilized in peptide synthesis. Especially preferred are those amino protecting groups which are cleavable under mildly acidic conditions from about pH=2 to 3. Particularly preferred amino protecting groups include t-butyl carbamate (BOC), benzyl carbamate (CBZ), and 9-flurorenylmethyl carbamate (FMOC).

The heteroaromatic ring defined by R³ can be an unsubstituted or mono-substituted five- or six-membered heteroaromatic ring having from 1 to 3 heteroatoms selected from the group consisting of oxygen, nitrogen, or sulfur and connected by a ring carbon to the amine of the amide group shown. The heteroaromatic ring contains a first nitrogen heteroatom adjacent to the connecting ring carbon atom, and if present, the other heteroatom(s) can be sulfur, oxygen, or nitrogen. Such heteroaromatic rings include, for example, pyridazinyl, isoxazolyl, isothiazolyl, and pyrazolyl. Among the preferred heteroaromatic rings are pyridinyl and thiazolyl. These heteroaromatic rings which constitute R³ are connected via a ring carbon atom to the amide group to form the amides of formula I. The ring carbon atom of the heteroaromatic ring which is connected via the amide linkage to form the compound of formula I cannot have any substituent.

When R³ is an unsubstituted or mono-substituted five-membered heteroaromatic ring, the preferred rings are those which contain a nitrogen heteroatom adjacent to the connecting ring carbon and a second heteroatom adjacent to the connecting ring carbon or adjacent to said first heteroatom. The preferred five-membered heteroaromatic rings contain 2 or 3 heteroatoms with thiazolyl, imidazolyl, oxazolyl, and thiadiazolyl being especially preferred. When the heteroaromatic ring is a six-membered heteroaromatic, the ring is connected by a ring carbon to the amine group shown, with one nitrogen heteroatom being adjacent to the connecting ring carbon atom. The preferred six-membered heteroaromatic rings include, for example, pyridinyl, pyrimidinyl, pyrazinyl, pyridazinyl, and triazinyl.

The term "pharmaceutically acceptable salts" as used herein include any salt with both inorganic or organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, para-toluene sulfonic acid and the like. The term "pharmaceutically acceptable salts" also includes any pharmaceutically acceptable base salt such as amine salts, trialkyl amine salts and the like. Such salts can be formed quite readily by those skilled in the art using standard techniques.

The compound of formula I can be prepared according to the following Reaction Scheme:

Reaction Scheme

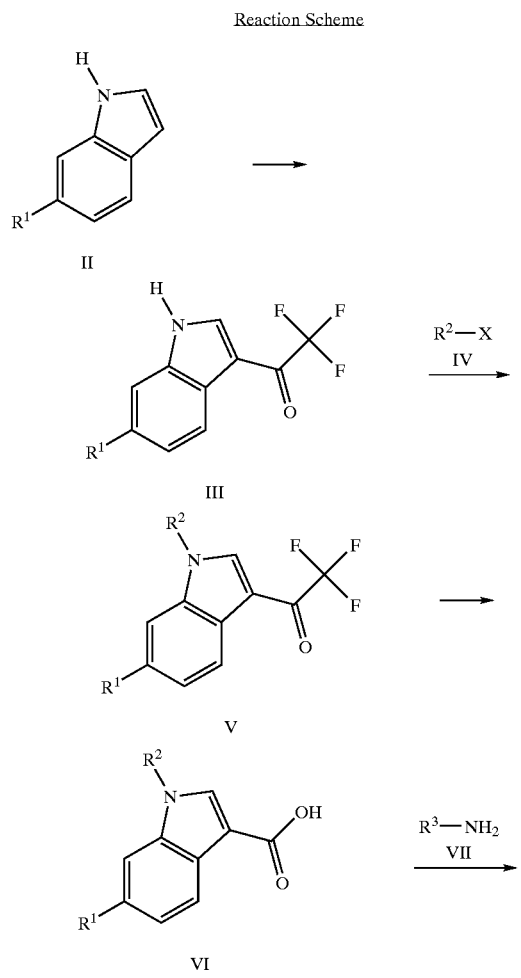

-continued

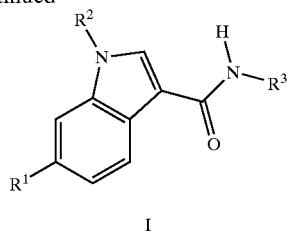

I wherein $R^1$, $R^2$, and $R^3$ are as above, and X is a halogen, preferably iodo or bromo.

In the first step of this Reaction Scheme, an indole compound of formula II is converted into the corresponding 3-trifluoroacetylindole compound of formula III by treatment with trifluoroacetic anhydride in a polar, water-miscible solvent such as tetrahydrofuran or N,N-dimethylformamide (*J. Chem. Soc.* 1954, 1651–1653; *Org. Prep. Proc. Int.* 1970, 2, 297–303).

The 3-trifluoroacetylindole compound of formula III can then be reacted with the alkyl halide of formula IV to produce the N-alkylated compound of formula V. This reaction can be carried out by any conventional means of N-alkylation of an indole. The preferred conditions for N-alkylation of the 3-trifluoroacetylindole compound of formula III include deprotonation of the indole-NH with excess potassium carbonate in N,N-dimethylformamide followed by treatment with the desired alkyl halide and then subsequent heating of the reaction mixture at high temperatures, from 60° C. to 75° C. being preferred.

The N-alkylated 3-trifluoroacetylindole compound of formula V can then be converted to the N-alkylated indole-3-carboxylic acid compound of formula VI. The compound of formula V readily undergoes a haloform cleavage reaction with 20% aqueous sodium hydroxide under refluxing conditions to afford the desired indole-3-carboxylic acid compound of formula VI (*J. Chem. Soc.* 1954, 1651–1653; *Org. Prep. Proc. Int.* 1970, 2, 297–303).

The compound of formula VI is then condensed with the compound of formula VII via conventional peptide coupling to produce the desired compound of formula I. In carrying out this reaction, any conventional method of condensing a primary amine with a carboxylic acid can be utilized to effect this conversion.

The indoles of formula II wherein $R^1$ is chloro [6-chloroindole], fluoro [6-fluoroindole], bromo [6-bromoindole], nitro [6-nitroindole], amino [6-aminoindole], cyano [6-cyanoindole], methyl [6-methylindole], trifluoromethyl [6-(trifluoromethyl)indole], hydroxy [6-hydroxyindole], methoxy [6-methoxyindole], and benzyloxy [6-benxyloxyindole] are commercially available.

The indoles of formula II wherein $R^1$ is trifluoromethoxy, methylthio, and iodo can be prepared from those skilled in the art by using synthetic transformations reported in the chemical literature: (a) 6-(trifluoromethoxy)indole, *J. Med. Chem.* 1998, 41(10), 1598–1612; (b) 6-(methylthio)indole, PCT Int. Appl. (1998), WO 9804553 A1; and (c) 6-iodoindole, *Heterocycles* 1987, 26(11), 2817–2822.

The indoles of formula II wherein $R^1$ is amino and hydroxy must be protected before carrying out the Reaction Scheme. The amino group and hydroxy group can be protected with any conventional acid removable group. The protecting groups are then removed from the amine and hydroxy groups after the step of coupling the compound of formula VI with the amine of formula VII to produce the desired compounds of formula I.

Once the compounds of formula I wherein $R^1$ is methylthio are available, they can be converted to the corresponding compounds of formula I wherein $R^1$ is methylsulfinyl. Any conventional method of oxidizing a methylthio substituent to a methylsulfinyl substituent (sulfoxide) can be utilized to effect this conversion. On the otherhand, if it is desired to produce compounds of formula I wherein $R^1$ is methylsulfonyl, the compounds of formula I wherein $R^1$ is methylthio can also be used as starting materials. Any conventional method of oxidizing a methylthio substituent to methylsulfonyl substituent can be utilized to effect this conversion.

The amino heteroaromatic compounds of formula VII are commercially available, or are known in the chemical literature, or can be prepared from those skilled in the art by using adaptations of standard synthetic transformations reported in the chemical literature. To produce the compounds of formula I, the synthetic conversions described herein to produce the desired $R^3$ substituents can take place either before or after the compounds of formula VII are converted to the compounds of formula I.

For example, the amino heteroaromatic compounds of formula VII, wherein one of the substitutions is —$(CH_2)_n COOR^5$ and where n=0 or 1 and $R^5$ is hydrogen or lower alkyl, can be prepared from the corresponding carboxylic acids —$(CH_2)_n COOR^5$ (n=0 and $R^5$ is hydrogen). Any conventional carbon homologation method can be utilized to convert a lower carboxylic acid to its higher homologs (see for example, Skeean, R. W.; Goel, O. P. Synthesis, 1990, 628), which in turn can then can be converted to the corresponding lower alkyl esters using any conventional esterification methods. The amino heteroaromatic compounds of formula VII, wherein one of the substitutions is —$(CH_2)_n C(=O)NHR^5$ and where n=0 or 1 and $R^5$ is hydrogen or lower alkyl, can in turn be made by the above mentioned carboxylic acids. Any conventional means of converting carboxylic acids to the corresponding amides may be utilized to effect this conversion. In turn, the lower alkyl amides can be converted to the corresponding amines of formula VII, wherein one of the substitutions is —$(CH_2)_n NHR^5$ and where n=1, by any conventional amide reduction method. The amino heteroaromatic compounds of formula VII, wherein one of the claimed substitutions is —$(CH_2)_n OR^5$ and where n=1, can be prepared from the above said corresponding lower alkyl esters. The lower alkyl esters can be converted to the corresponding alcohols using any conventional ester reduction method.

Such amines and alcohols described above would have to be selectively protected before carrying out the condensation step. The amino group and alcohol group can be protected with any conventional acid removable group. The protecting groups are then removed from the amine and alcohol groups after the coupling step to produce the desired compounds of formula I.

If it is desired to produce the amino heteroaromatic compounds of formula VII wherein one of the substituents is cyano or the compound of formula I wherein one of the substituents on the five- or six-membered heteroaromatic ring is cyano, then the corresponding halogen (especially bromo) can be utilized as the starting material. Any conventional method of converting a halogen to a cyanide may be utilized to effect this conversion.

All of the compounds of formula I, which include the compounds set forth in the Examples, activated glucokinase in vitro by the procedure of Example A. In this manner, they increase the flux of glucose metabolism, which causes increased insulin secretion. Therefore, the compounds of formula I are glucokinase activators useful for increasing insulin secretion.

The present invention encompasses the following examples.

EXAMPLE 1

1-Isopropyl-6-methyl-1H-indole-3-carboxylic acid thiazol-2-ylamide

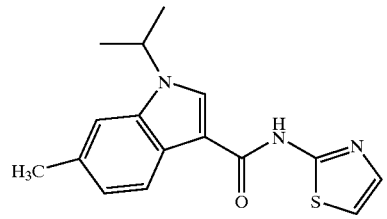

A solution of 6-methyl-1H-indole (1.0 g, 7.62 mmol) in tetrahydrofuran (10 mL) cooled to 0° C. was treated with trifluoroacetic anhydride (1.62 mL, 11.43 mmol). The reaction was stirred at 0° C. for 1 h. At this time, the resulting precipitate was collected by filtration, washed with water, and dried in vacuo to afford 2,2,2-trifluoro-1-(6-methyl-1H-indol-3-yl)-ethanone (146 mg, 8%) as a white solid: mp 216–218° C.; EI-HRMS m/e calcd for $C_{11}H_8F_3NO$ ($M^+$) 227.0558, found 227.0554.

A solution of 2,2,2-trifluoro-1-(6-methyl-1H-indol-3-yl)-ethanone (1.5 g, 6.60 mmol) in N,N-dimethylformamide (15 mL) at 25° C. was treated with potassium carbonate (2.28 g, 16.51 mmol). The resulting mixture was stirred at 25° C. for 15 min and then treated with 2-iodopropane (0.99 mL, 9.90 mmol). The reaction was heated at 65° C. for 3 h. At this time, the reaction was cooled to 25° C. and was partitioned between water (100 mL) and ethyl acetate (100 mL). The organic layer was then washed with a 1N aqueous hydrochloric acid solution (1×50 mL) and a saturated aqueous sodium chloride solution (1×50 mL), dried over magnesium sulfate, filtered, and concentrated in vacuo. Biotage chromatography (FLASH 40M, Silica, 4/1 hexanes/ethyl acetate) afforded 2,2,2-trifluoro-1-(1-isopropyl-6-methyl-1H-indol-3-yl)-ethanone (1.61 g, 90.6%) as a pink solid: mp 65–68° C.; EI-HRMS m/e calcd for $C_{14}H_{14}F_3NO$ ($M^+$) 269.1027, found 269.1037.

A solution of 2,2,2-trifluoro-1-(1-isopropyl-6-methyl-1H-indol-3-yl)-ethanone (1.50 g, 5.57 mmol) in a 20% aqueous sodium hydroxide solution (20 mL) was heated at 110° C. for 18 h. At this time, the reaction was cooled to 25° C., partitioned between water (150 mL) and ethyl acetate (150 mL), and then treated with a 1N aqueous hydrochloric acid solution (50 mL). The organic layer was washed with a saturated aqueous sodium bicarbonate solution (1×50 mL), water (1×50 mL), and a saturated aqueous sodium chloride solution (1×50 mL). The organic layer was then dried over magnesium sulfate, filtered, and concentrated in vacuo to afford 1-isopropyl-6-methyl-1H-indole-3-carboxylic acid (1.19 g, 98%) as a yellow solid: mp 185–186° C.; EI-HRMS m/e calcd for $C_{13}H_{15}NO_2$ ($M^+$) 217.1103, found 217.1110.

A solution of triphenylphosphine (628 mg, 2.39 mmol) in methylene chloride (5 mL) cooled to 0° C. was treated with N-bromosuccinimide (425 mg, 2.39 mmol). The reaction was stirred at 0° C. for 15 min and then was treated with 1-isopropyl-6-methyl-1H-indole-3-carboxylic acid (400 mg, 1.84 mmol). The reaction was stirred at 0° C. for 15 min and then was allowed to warm to 25° C. where it was stirred for 30 min. The reaction was then treated with 2-aminothiazole (424 mg, 4.23 mmol) and stirred at 25° C. for 16 h. At this time, the mixture was partitioned between water (75 mL) and ethyl acetate (75 mL) and treated with a 1N aqueous hydrochloric acid solution (40 mL). The organic layer was washed with a saturated aqueous sodium bicarbonate solution (1×40 mL) and a saturated aqueous sodium chloride solution (1×40 mL), dried over magnesium sulfate, filtered, and concentrated in vacuo. Biotage chromatography (FLASH 40M, Silica, 1/1 hexanes/ethyl acetate) afforded 1-isopropyl-6-methyl-1H-indole-3-carboxylic acid thiazol-2-ylamide (229 mg, 41.5%) as a tan solid: mp 215–217° C.; EI-HRMS m/e calcd for $C_{16}H_{17}N_3OS$ (M$^+$) 363.0041, found 363.0034.

EXAMPLE 2

1-Isopropyl-6-trifluoromethyl-1H-indole-3-carboxylic acid thiazol-2-ylamide

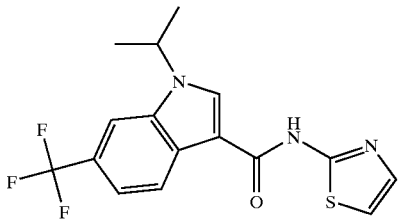

A solution of 6-trifluoromethyl-1H-indole (2.0 g, 10.80 mmol) in tetrahydrofuran (10 mL) cooled to 0° C. was treated with trifluoroacetic anhydride (2.29 mL, 16.20 mmol). The reaction was stirred at 0° C. for 1 h and then allowed to warm to 25° C. where it was stirred for 16 h. At this time, the reaction was poured into water (150 mL) and was stirred at 25° C. for 5 min. The resulting precipitate was collected by filtration, washed with water (200 mL), and dried in vacuo to afford 2,2,2-trifluoro-1-(6-trifluoromethyl-1H-indol-3-yl)-ethanone (2.95 g, 97%) as a white solid: mp 250–251° C.; EI-HRMS m/e calcd for $C_{11}H_5F_6NO$ (M$^+$) 281.0275, found 281.0266.

A solution of 2,2,2-trifluoro-1-(6-trifluoromethyl-1H-indol-3-yl)-ethanone (1.0 g, 3.56 mmol) in N,N-dimethylformamide (10 mL) at 25° C. was treated with potassium carbonate (1.22 g, 8.89 mmol). The resulting mixture was stirred at 25° C. for 10 min. At this time, the reaction was treated with 2-iodopropane (0.53 mL, 5.34 mmol). The reaction was heated at 65° C. for 4 h. At this time, the reaction was cooled to 25° C. and was partitioned between water (75 mL) and ethyl acetate (75 mL). The organic layer was washed with a 1N aqueous hydrochloric acid solution (1×25 mL), water (1×50 mL), and a saturated aqueous sodium chloride solution (1×50 mL). The organic layer was then dried over magnesium sulfate, filtered, and concentrated in vacuo to afford 2,2,2-trifluoro-1-(1-isopropyl-6-trifluoromethyl-1H-indol-3-yl)-ethanone (850 mg, 74%) as a pale orange solid: mp 92–93° C.; EI-HRMS m/e calcd for $C_{14}H_{11}F_6NO$ (M$^+$) 323.0745, found 323.0739.

A solution of 2,2,2-trifluoro-1-(1-isopropyl-6-trifluoromethyl-1H-indol-3-yl)-ethanone (800 mg, 2.48 mmol) in a 20% aqueous sodium hydroxide solution (12 mL) was heated at 110° C. for 3 h. At this time, the reaction was cooled to 25° C., partitioned between water (100 mL) and ethyl acetate (100 mL), and treated with a 1N aqueous hydrochloric acid solution (50 mL). The organic layer was dried over magnesium sulfate, filtered, and concentrated in vacuo to afford 1-isopropyl-6-trifluoromethyl-1H-indole-3-carboxylic acid (704 mg, 99%) as a yellow solid: mp 177–178° C.; EI-HRMS m/e calcd for $C_{13}H_{12}F_3NO_2$ (M$^+$) 271.0820, found 271.0807.

A solution of triphenylphosphine (377 mg, 1.44 mmol) in methylene chloride (4 mL) cooled to 0° C. was treated with N-bromosuccinimide (256 mg, 1.44 mmol). The reaction was stirred at 0° C. for 15 min. At this time, the reaction was treated with 1-isopropyl-6-trifluoromethyl-1H-indole-3-carboxylic acid (300 mg, 1.11 mmol). The reaction was stirred at 0° C. for 5 min and then was allowed to warm to 25° C. where it was stirred for 30 min. The reaction was then treated with 2-aminothiazole (255 mg, 2.54 mmol) and stirred at 25° C. for 24 h. At this time, the mixture was partitioned between water (50 mL) and ethyl acetate (50 mL) and treated with a 1N aqueous hydrochloric acid solution (25 mL). The organic layer was washed with a saturated aqueous sodium bicarbonate solution (1×25 mL) and a saturated aqueous sodium chloride solution (1×25 mL), dried over magnesium sulfate, filtered, and concentrated in vacuo. Biotage chromatography (FLASH 40S, Silica, diethyl ether) afforded 1-isopropyl-6-trifluoromethyl-1H-indole-3-carboxylic acid thiazol-2-ylamide (43 mg, 11%) as a light pink solid: mp 246–247° C.; EI-HRMS m/e calcd for $C_{16}H_{14}F_3N_3OS$ (M$^+$) 353.0810, found 353.0801.

EXAMPLE 3

1-Isopropyl-6-nitro-1H-indole-3-carboxylic acid thiazol-2-ylamide

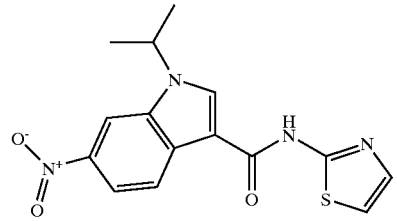

A solution of 6-nitro-1H-indole (1.0 g, 6.17 mmol) in tetrahydrofuran (5 mL) cooled to 0° C. was treated with trifluoroacetic anhydride (1.31 mL, 9.25 mmol). The reaction was stirred at 0° C. for 1 h and then was allowed to warm to 25° C. where it was stirred for 16 h. At this time, the reaction was poured into water (100 mL) and stirred at 25° C. for 5 min. The resulting precipitate was collected by filtration, washed with water (100 mL), and dried in vacuo. This solid was re-dissolved in tetrahydrofuran (8 mL) at 25° C., and the resulting solution was treated with trifluoroacetic anhydride (1 mL, 7.08 mmol) and was stirred at 25° C. for 1 h. The resulting precipitate was collected by filtration, washed with water, and dried in vacuo to afford 2,2,2-trifluoro-1-(6-nitro-1H-indol-3-yl)-ethanone (646 mg, 40%) as a yellow solid: mp 263–265° C.; EI-HRMS m/e calcd for $C_{10}H_5F_3N_2O_3$ (M$^+$) 258.0252, found 258.0253.

A solution of 2,2,2-trifluoro-1-(6-nitro-1H-indol-3-yl)-ethanone (1.0 g, 3.87 mmol) in N,N-dimethylformamide (10 mL) at 25° C. was treated with potassium carbonate (1.34 g, 9.68 mmol). The resulting mixture was stirred at 25° C. for 10 min and then treated with 2-iodopropane (0.58 mL, 5.81 mmol). The reaction was heated at 65° C. for 3 h. At this time, the reaction was cooled to 25° C. and was partitioned between water (50 mL) and ethyl acetate (50 mL). This mixture was treated with a 1N aqueous hydrochloric acid solution (25 mL). The organic layer was washed with water (1×50 mL) and a saturated aqueous sodium chloride solution (1×50 mL), dried over magnesium sulfate, filtered, and concentrated in vacuo to afford 2,2,2-trifluoro-1-(1-isopropyl-6-nitro-1H-indol-3-yl)-ethanone (581 mg, 98%) as a yellow solid: mp 143–145° C.; EI-HRMS m/e calcd for $C_{14}H_{14}F_3NO$ ($M^+$) 269.1027, found 269.1037.

A solution of 2,2,2-trifluoro-1-(1-isopropyl-6-nitro-1H-indol-3-yl)-ethanone (525 mg, 1.75 mmol) in a 20% aqueous sodium hydroxide solution (10 mL) was heated at 1110° C. for 2 h. At this time, the reaction was cooled to 25° C., partitioned between water (75 mL) and ethyl acetate (75 mL), and treated with a 1N aqueous hydrochloric acid solution (25 mL). The organic layer was washed with water (1×50 mL) and a saturated aqueous sodium chloride solution (1×50 mL), dried over magnesium sulfate, filtered, and concentrated in vacuo to afford 1-isopropyl-6-nitro-1H-indole-3-carboxylic acid (436 mg, 99%) as a yellow solid: mp 242–243° C.; EI-HRMS m/e calcd for $C_{12}H_{12}N_2O_4$ ($M^+$) 248.0797, found 248.0796.

A solution of 1-isopropyl-6-nitro-1H-indole-3-carboxylic acid (200 mg, 0.81 mmol) in methylene chloride (4 mL) and N,N-diisopropylethylamine (0.32 mL, 1.85 mmol) at 25° C. was treated with benzotriazol-1-yloxy-tris(dimethylamino) phosphonium hexafluoro-phosphate (463 mg, 1.05 mmol). The reaction was stirred at 25° C. for 20 min. At this time, the reaction was treated with 2-aminothiazole (186 mg, 1.85 mmol) and was stirred at 25° C. for 24 h. At this time, the reaction mixture was partitioned between water (50 mL) and ethyl acetate (50 mL) and was treated with a 1N aqueous hydrochloric acid solution (25 mL). The organic layer was washed with a saturated aqueous sodium chloride solution, dried over magnesium sulfate, filtered, and concentrated in vacuo. The resulting solid was dissolved in a hot solution of 1/1 hexanes/ethyl acetate and then filtered. The filtrate was cooled in the freezer for 1 h. At this time, the resulting solid was collected by filtration. The filtrate was concentrated in vacuo. Biotage chromatography (FLASH 40S, Silica, 1/1 hexanes/ethyl acetate) afforded 1-isopropyl-6-nitro-1H-indole-3-carboxylic acid thiazol-2-ylamide (13 mg, 4.9%) as a yellow solid: mp 236–239° C.; EI-HRMS m/e calcd for $C_{15}H_{14}N_4O_3S$ ($M^+$) 330.0786, found 330.0792.

EXAMPLE 4

6-Hydroxy-1-isopropyl-1H-indole-3-carboxylic acid thiazol-2-ylamide

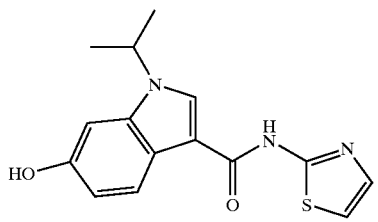

A solution of 6-methoxy-1H-indole (927 mg, 6.30 mmol) in tetrahydrofuran (5 mL) cooled to 0° C. was treated with trifluoroacetic anhydride (1.33 mL, 9.45 mmol) followed by additional tetrahydrofuran (3 mL). The reaction was stirred at 0° C. for 30 min. At this time, the reaction was poured into water (75 mL). The resulting precipitate was collected by filtration, washed with water, and dried in vacuo to afford 2,2,2-trifluoro-1-(6-methoxy-1H-indol-3-yl)-ethanone (1.56 g, 94.5%) as a yellow solid: mp 206–208° C.; EI-HRMS m/e calcd for $C_{11}H_8F_3NO_2$ ($M^+$) 243.0507, found 243.0515.

A solution of 2,2,2-trifluoro-1-(6-methoxy-1H-indol-3-yl)-ethanone (1.0 g, 4.11 mmol) in N,N-dimethylformamide (10 mL) at 25° C. was treated with potassium carbonate (1.42 mg, 10.28 mmol). The resulting mixture was stirred at 25° C. for 30 min and then was treated with 2-iodopropane (0.62 mL, 6.17 mmol). The reaction was heated at 65° C. for 20 h. At this time, the reaction was cooled to 25° C. and was partitioned between water (50 mL) and ethyl acetate (50 mL). This mixture was treated with a 1N aqueous hydrochloric acid solution (25 mL), shaken, and separated. The organic layer was washed with water (1×50 mL) and a saturated aqueous sodium chloride solution (1×50 mL), dried over magnesium sulfate, filtered, and concentrated in vacuo. Biotage chromatography (FLASH 40M, Silica, 3/1 hexanes/ethyl acetate) afforded 2,2,2-trifluoro-1-(1-isopropyl-6-methoxy-1H-indol-3-yl)-ethanone (99 mg, 85%) as a yellow solid: mp 58–60° C.; EI-HRMS m/e calcd for $C_{14}H_{14}F_3NO_2$ ($M^+$) 285.0977, found 285.0974.

A solution of 2,2,2-trifluoro-1-(1-isopropyl-6-methoxy-1H-indol-3-yl)-ethanone (950 mg, 3.33 mmol) in a 20% aqueous sodium hydroxide solution (12 mL) was heated at 105° C. for 18 h. At this time, the reaction was cooled to 25° C., partitioned between water (50 mL) and ethyl acetate (50 mL), and treated with a 1N aqueous hydrochloric acid solution (35 mL). The organic layer was dried over magnesium sulfate, filtered, and concentrated in vacuo. The resulting solids were collected by filtration, washed with petroleum ether, and dried in vacuo to afford 1-isopropyl-6-methoxy-1H-indole-3-carboxylic acid (553 mg, 71%) as orange needles: mp 162–163° C.; EI-HRMS m/e calcd for $C_{13}H_{15}NO_3$ ($M^+$) 233.1052, found 233.1056.

A solution of triphenylphosphine (219 mg, 0.84 mmol) in methylene chloride (3 mL) cooled to 0° C. was treated with N-bromosuccinimide (149 mg, 0.84 mmol). The reaction was stirred at 0° C. for 15 min. At this time, the reaction was treated with 1-isopropyl-6-methoxy-1H-indole-3-carboxylic acid (150 mg, 0.64 mmol). The reaction was stirred at 0° C. for 5 min and then was allowed to warm to 25° C. where it was stirred for 30 min. The reaction was then treated with 2-aminothiazole (148 mg, 1.48 mmol) and stirred at 25° C. for 24 h. At this time, the mixture was partitioned between water (50 mL) and ethyl acetate (50 mL) and treated with a 1N aqueous hydrochloric acid solution (25 mL). The organic layer was washed with a saturated aqueous sodium bicarbonate solution (1×25 mL) and a saturated aqueous sodium chloride solution (1×25 mL). The organic layer was then dried over magnesium sulfate, filtered, and concentrated in vacuo. Biotage chromatography (FLASH 40S, Silica, 1/1 hexanes/ethyl acetate) afforded 1-isopropyl-6-methoxy-1H-indole-3-carboxylic acid thiazol-2-ylamide (101 mg, 50%) as tan solid: mp 182–185° C.; EI-HRMS m/e calcd for $C_{16}H_{17}N_3O_2S$ ($M^+$) 315.1041, found 315.1039.

A 1.0M solution of boron tribromide in methylene chloride (2.70 mL, 2.70 mmol) at 25° C. was treated with a solution of 1-isopropyl-6-methoxy-1H-indole-3-carboxylic acid thiazol-2-ylamide (85 mg, 0.27 mmol) in methylene chloride (2.7 mL). The reaction was stirred at 25° C. for 1 h. At this time, the reaction was cooled to 0° C. and then was treated with a 20% aqueous ammonium hydroxide solution (3 mL). The reaction mixture was stirred at 0° C. for 15 min. At this time, the resulting precipitate was collected by filtration to afford (6-hydroxy-1-isopropyl-1H-indole-3-carboxylic acid thiazol-2-ylamide (31.9 mg, 39%) as a yellow solid: mp 239–241° C.; EI-HRMS m/e calcd for $C_{15}H_{15}N_3O_2S$ (M) 315.1041, found 315.1039.

EXAMPLE 5

1-Isopropyl-6-methoxy-1H-indole-3-carboxylic acid thiazol-2-ylamide

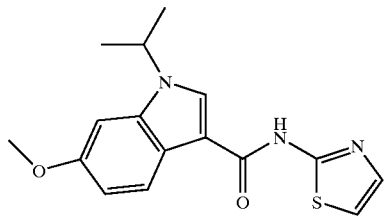

A solution of 6-methoxy-1H-indole (927 mg, 6.30 mmol) in tetrahydrofuran (5 mL) cooled to 0° C. was treated with trifluoroacetic anhydride (1.33 mL, 9.45 mmol) followed by additional tetrahydrofuran (3 mL). The reaction was stirred at 0° C. for 30 min. At this time, the reaction was poured into water (75 mL). The resulting precipitate was collected by filtration, washed with water, and dried in vacuo to afford 2,2,2-trifluoro-1-(6-methoxy-1H-indol-3-yl)-ethanone (1.56 g, 94.5%) as a yellow solid: mp 206–208° C.; EI-HRMS m/e calcd for $C_{11}H_8F_3NO_2$ (M+) 243.0507, found 243.0515.

A solution of 2,2,2-trifluoro-1-(6-methoxy-1H-indol-3-yl)-ethanone (1.0 g, 4.11 mmol) in N,N-dimethylformamide (10 mL) at 25° C. was treated with potassium carbonate (1.42 mg, 10.28 mmol). The resulting mixture was stirred at 25° C. for 30 min and then was treated with 2-iodopropane (0.62 mL, 6.17 mmol). The reaction was heated at 65° C. for 20 h. At this time, the reaction was cooled to 25° C. and was partitioned between water (50 mL) and ethyl acetate (50 mL). This mixture was treated with a 1N aqueous hydrochloric acid solution (25 mL), shaken, and separated. The organic layer was washed with water (1×50 mL) and a saturated aqueous sodium chloride solution (1×50 mL), dried over magnesium sulfate, filtered, and concentrated in vacuo. Biotage chromatography (FLASH 40M, Silica, 3/1 hexanes/ethyl acetate) afforded 2,2,2-trifluoro-1-(1-isopropyl-6-methoxy-1H-indol-3-yl)-ethanone (99 mg, 85%) as a yellow solid: mp 58–60° C.; EI-HRMS m/e calcd for $C_{14}H_{14}F_3NO_2$ (M+) 285.0977, found 285.0974.

A solution of 2,2,2-trifluoro-1-(1-isopropyl-6-methoxy-1H-indol-3-yl)-ethanone (950 mg, 3.33 mmol) in a 20% aqueous sodium hydroxide solution (12 mL) was heated at 105° C. for 18 h. At this time, the reaction was cooled to 25° C., partitioned between water (50 mL) and ethyl acetate (50 mL), and treated with a 1N aqueous hydrochloric acid solution (35 mL). The organic layer was dried over magnesium sulfate, filtered, and concentrated in vacuo. The resulting solids were collected by filtration, washed with petroleum ether, and dried in vacuo to afford 1-isopropyl-6-methoxy-1H-indole-3-carboxylic acid (553 mg, 71%) as orange needles: mp 162–163° C.; EI-HRMS m/e calcd for $C_{13}H_{15}NO_3$ (M+) 233.1052, found 233.1056.

A solution of triphenylphosphine (219 mg, 0.84 mmol) in methylene chloride (3 mL) cooled to 0° C. was treated with N-bromosuccinimide (149 mg, 0.84 mmol). The reaction was stirred at 0° C. for 15 min. At this time, the reaction was treated with 1-isopropyl-6-methoxy-1H-indole-3-carboxylic acid (150 mg, 0.64 mmol). The reaction was stirred at 0° C. for 5 min and then was allowed to warm to 25° C. where it was stirred for 30 min. The reaction was then treated with 2-aminothiazole (148 mg, 1.48 mmol) and stirred at 25° C. for 24 h. At this time, the mixture was partitioned between water (50 mL) and ethyl acetate (50 mL) and treated with a 1N aqueous hydrochloric acid solution (25 mL). The organic layer was washed with a saturated aqueous sodium bicarbonate solution (1×25 mL) and a saturated aqueous sodium chloride solution (1×25 mL). The organic layer was then dried over magnesium sulfate, filtered, and concentrated in vacuo. Biotage chromatography (FLASH 40S, Silica, 1/1 hexanes/ethyl acetate) afforded 1-isopropyl-6-methoxy-1H-indole-3-carboxylic acid thiazol-2-ylamide (101 mg, 50%) as a tan solid: mp 182–185° C.; EI-HRMS m/e calcd for $C_{16}H_{17}N_3O_2S$ (M+) 315.1041, found 315.1039.

EXAMPLE 6

1-Isopropyl-6-methylsulfanyl-1H-indole-3-carboxylic acid thiazol-2-ylamide

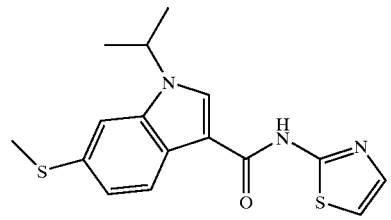

A mixture of potassium hydride in mineral oil (35 wt. %, 3.04 g, 26.52 mmol) in tetrahydrofuran (53 mL) was cooled to 0° C. then was treated with a solution of 6-bromo-1H-indole (5.20 g, 26.52 mmol) in tetrahydrofuran (53 mL). The reaction was stirred at 0° C. for 30 min. At this time, the reaction was cooled to −78° C. and was treated with a 1.7M solution of tert-butyllithium in pentane (31.2 mL, 53.04 mmol). The reaction mixture was stirred at −78° C. for 20 min. At this time, the reaction was added to a solution of methyl disulfide (4.78 mL, 53.04 mmol) in tetrahydrofuran (15 mL). The reaction was then allowed to warm to 25° C. where it was stirred for 18 h. The reaction was then quenched by the addition of a saturated aqueous ammonium chloride solution (300 mL) and was extracted with ethyl acetate (1×500 mL). The organic layer was washed with a saturated aqueous sodium chloride solution (1×300 mL), dried over magnesium sulfate, filtered, and concentrated in vacuo. Flash chromatography (Merck Silica gel 60, 230–400 mesh, 9/1 hexanes/ethyl acetate) afforded 6-methylsulfanyl-1H-indole (2.3 g, 53%) as an off-white solid: mp 88–90° C.; EI-HRMS m/e calcd for $C_9H_9NS$ (M+) 163.0456, found 163.0457.

A solution of 6-methylsulfanyl-1H-indole (1.30 g, 7.96 mmol) in tetrahydrofuran (5 mL) cooled to 0° C. was treated with trifluoroacetic anhydride (1.69 mL, 11.94 mmol) followed by additional tetrahydrofuran (5 mL). The reaction was stirred at 0° C. for 30 min and then was allowed to warm to 25° C. At this time, the reaction was poured into water (50 mL) and was stirred at 25° C. for 30 min. The resulting precipitate was collected by filtration and dried in vacuo. Due to the presence of approximately 10% unreacted 6-methylsulfanyl-1H-indole, the resulting solid was slurried in tetrahydrofuran (5 mL) and re-treated with trifluoroacetic anhydride (1.12 mL, 7.96 mmol). The reaction mixture was stirred at 25° C. for 2 d. At this time, the resulting solids were collected by filtration, washed with petroleum ether, and dried in vacuo to afford 2,2,2-trifluoro-1-(6-methylsulfanyl-1H-indol-3-yl)-ethanone (1.03 g, 50%) as a yellow solid: mp 237–239° C.; EI-HRMS m/e calcd for $C_{11}H_9F_3NOS$ (M+) 259.0279, found 259.0270.

A solution of 2,2,2-trifluoro-1-(6-methylsulfanyl-1H-indol-3-yl)-ethanone (200 mg, 0.77 mmol) in N,N-dimethylformamide (2 mL) at 25° C. was treated with potassium carbonate (160 mg, 1.16 mmol). The reaction was stirred at 25° C. for 15 min and then was treated with 2-iodopropane (0.11 mL, 1.16 mmol). The reaction was stirred at 25° C. for 18 h and then was heated at 60° C. for 2 h. At this time, the reaction was cooled to 25° C. and was partitioned between water (50 mL) and ethyl acetate (50 mL). The layers were separated. The aqueous layer was extracted with ethyl acetate (1×50 mL). The organic layer was dried over magnesium sulfate, filtered, and concentrated in vacuo. Biotage chromatography (FLASH 40S, Silica, 3/1 hexanes/ethyl acetate) afforded 2,2,2-trifluoro-1-(1-isopropyl-6-methylsulfanyl-1H-indol-3-yl)-ethanone (216 mg, 93%) as an off-white solid: mp 67–69° C.; (ES)+-HRMS m/e calcd for $C_{14}H_{14}F_3NOS$ (M+) 301.0748, found 301.0740.

A solution of 2,2,2-trifluoro-1-(1-isopropyl-6-methylsulfanyl-1H-indol-3-yl)-ethanone (200 mg, 0.77 mmol) in tetrahydrofuran (1 mL) at 25° C. was treated with a 20% aqueous sodium hydroxide solution (2 mL). The mixture was heated at 100° C. for 24 h. At this time, the reaction was cooled to 25° C. and was partitioned between water (40 mL) and ethyl acetate (40 mL). The solution was treated with a 1N aqueous hydrochloric acid solution. The layers were then shaken and separated. The organic layer was dried over magnesium sulfate, filtered, and concentrated in vacuo. Biotage chromatography (FLASH 40S, Silica, 2/1 hexanes/ethyl acetate) afforded 1-isopropyl-6-methylsulfanyl-1H-indole-3-carboxylic acid (126 mg, 77%) as a white solid: mp 132–133° C.; EI-HRMS m/e calcd for $C_{13}H_{15}NO_2S$ (M+) 249.0823, found 249.0819.

A solution of 1-isopropyl-6-methylsulfanyl-1H-indole-3-carboxylic acid (275 mg, 1.10 mmol) and benzotriazol-1-yloxy-tris(dimethylamino)phosphonium hexafluorophosphate (585 mg, 1.32 mmol) in methylene chloride (5 mL) at 25° C. was treated with N,N-diisopropylethylamine (0.44 mL, 2.54 mmol). The reaction was stirred at 25° C. for 30 min. At this time, the reaction was treated with 2-aminothiazole (254 mg, 2.54 mmol) and then was stirred at 25° C. for 18 h. The reaction was then partitioned between water (40 mL) and ethyl acetate (40 mL) and was treated with a 1N aqueous hydrochloric acid solution (25 mL). The layers were shaken and separated. The organic layer was washed with a saturated aqueous sodium bicarbonate solution (1×25 mL), water (1×25 mL), and a saturated aqueous sodium chloride solution (1×25 mL). The organic layer was then dried over magnesium sulfate, filtered, and concentrated in vacuo. Biotage chromatography (FLASH 40S, Silica, 1/1 hexanes/ethyl acetate) afforded 1-isopropyl-6-methylsulfanyl-1H-indole-3-carboxylic acid thiazol-2-ylamide (155 mg, 42%) as light yellow solid: mp 172–176° C.; (ES)+-HRMS m/e calcd for $C_{16}H_{17}N_3OS_2$ (M+Na)+ 354.0705, found 354.0709.

EXAMPLE 7

1-Isopropyl-6-methanesulfonyl-1H-indole-3-carboxylic acid thiazol-2-ylamide

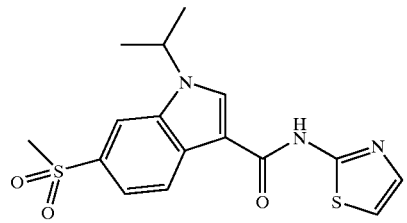

A mixture of potassium hydride in mineral oil (35 wt. %, 3.04 g, 26.52 mmol) in tetrahydrofuran (53 mL) was cooled to 0° C. then was treated with a solution of 6-bromo-1H-indole (5.20 g, 26.52 mmol) in tetrahydrofuran (53 mL). The reaction was stirred at 0° C. for 30 min. At this time, the reaction was cooled to −78° C. and then was treated with 1.7M solution of tert-butyllithium in pentane (31.2 mL, 53.04 mmol). The reaction mixture was stirred at −78° C. for 20 min. At this time, the reaction was added to a solution of methyl disulfide (4.78 mL, 53.04 mmol) in tetrahydrofuran (15 mL). The reaction was then allowed to warm to 25° C. where it was stirred for 18 h. At this time, the reaction was quenched by the addition of a saturated aqueous ammonium chloride solution (300 mL) and was extracted with ethyl acetate (1×500 mL). The organic layer was washed with a saturated aqueous sodium chloride solution (1×300 mL), dried over magnesium sulfate, filtered, and concentrated in vacuo. Flash chromatography (Merck Silica gel 60, 230–400 mesh, 9:1 hexanes/ethyl acetate) afforded 6-methylsulfanyl-1H-indole (2.3 g, 53%) as an off-white solid: mp 88–90° C.; EI-HRMS m/e calcd for $C_9H_9N_5$ (M+) 163.0456, found 163.0457.

A solution of 6-methylsulfanyl-1H-indole (1.30 g, 7.96 mmol) in tetrahydrofuran (5 mL) cooled to 0° C. was treated with trifluoroacetic anhydride (1.69 mL, 11.94 mmol) followed by additional tetrahydrofuran (5 mL). The reaction was stirred at 0° C. for 30 min and then was allowed to warm to 25° C. At this time, the reaction was poured into water (50 mL) and was stirred at 25° C. for 30 min. The resulting precipitate was collected by filtration and dried in vacuo. Due to the presence of approximately 10% unreacted 6-methylsulfanyl-1H-indole, the resulting solid was slurried in tetrahydrofuran (5 mL) and re-treated with trifluoroacetic anhydride (1.12 mL, 7.96 mmol). The reaction mixture was stirred at 25° C. for 2 d. At this time, the resulting solids were collected by filtration, washed with petroleum ether, and dried in vacuo to afford 2,2,2-trifluoro-1-(6-methylsulfanyl-1H-indol-3-yl)-ethanone (1.03 g, 50%) as a yellow solid: mp 237–239° C.; EI-HRMS m/e calcd for $C_{11}H_8F_3NOS$ (M+) 259.0279, found 259.0270.

A solution of 2,2,2-trifluoro-1-(6-methylsulfanyl-1H-indol-3-yl)-ethanone (200 mg, 0.77 mmol) in N,N-dimethylformamide (2 mL) at 25° C. was treated with potassium carbonate (160 mg, 1.16 mmol). The reaction was stirred at 25° C. for 15 min and then was treated with 2-iodopropane (0.11 mL, 1.16 mmol). The reaction was stirred at 25° C. for 18 h and then was heated at 60° C. for 2 h. At this time, the reaction was cooled to 25° C. and was partitioned between water (50 mL) and ethyl acetate (50 mL). The layers were separated. The aqueous layer was extracted with ethyl acetate (1×50 mL). The organic layer was dried over magnesium sulfate, filtered, and concentrated in vacuo. Biotage chromatography (FLASH 40S, Silica, 3/1 hexanes/ethyl acetate) afforded 2,2,2-trifluoro-1-(1-isopropyl-6-methylsulfanyl-1H-indol-3-yl)-ethanone (216 mg, 93%) as an off-white solid: mp 67–69° C.; (ES)+-HRMS m/e calcd for $C_{14}H_{14}F_3NOS$ (M+) 301.0748, found 301.0740.

A solution of 2,2,2-trifluoro-1-(1-isopropyl-6-methylsulfanyl-1H-indol-3-yl)-ethanone (200 mg, 0.77 mmol) in tetrahydrofuran (1 mL) at 25° C. was treated with a 20% aqueous sodium hydroxide solution (2 mL). The mixture was heated at 100° C. for 24 h. At this time, the reaction was cooled to 25° C. and was partitioned between water (40 mL) and ethyl acetate (40 mL). The solution was treated with a 1N aqueous hydrochloric acid solution. The layers were then shaken and separated. The organic layer was dried over magnesium sulfate, filtered, and concentrated in vacuo. Biotage chromatography (FLASH 40S, Silica, 2/1 hexanes/ethyl acetate) afforded 1-isopropyl-6-methylsulfanyl-1H-indole-3-carboxylic acid (126 mg, 77%) as a white solid: mp 132–133° C.; EI-HRMS m/e calcd for $C_{13}H_{15}NO_2S$ (M+) 249.0823, found 249.0819.

A solution of 1-isopropyl-6-methylsulfanyl-1H-indole-3-carboxylic acid (275 mg, 1.10 mmol) and benzotriazol-1-yloxy-tris(dimethylamino)phosphonium hexafluorophosphate (585 mg, 1.32 mmol) in methylene chloride (5 mL) at 25° C. was treated with N,N-diisopropylethylamine (0.44 mL, 2.54 mmol). The reaction was stirred at 25° C. for 30 min. At this time, the reaction was treated with 2-aminothiazole (254 mg, 2.54 mmol). The reaction was stirred at 25° C. for 18 h. At this time, the reaction was partitioned between water (40 mL) and ethyl acetate (40 mL) and was treated with a 1N aqueous hydrochloric acid solution (25 mL). The layers were shaken and separated. The organic layer was washed with a saturated aqueous sodium bicarbonate solution (1×25 mL), water (1×25 mL), and a saturated aqueous sodium chloride solution (1×25 mL). The organic layer was then dried over magnesium sulfate, filtered, and concentrated in vacuo. Biotage chromatography (FLASH 40S, Silica, 1/1 hexanes/ethyl acetate) afforded 1-isopropyl-6-methylsulfanyl-1H-indole-3-carboxylic acid thiazol-2-ylamide (155 mg, 42%) as light yellow solid: mp 172–176° C.; (ES)+-HRMS m/e calcd for $C_{16}H_{17}N_3OS_2$ (M+Na)+ 354.0705, found 354.0709.

A solution of 1-isopropyl-6-methylsulfanyl-1H-indole-3-carboxylic acid thiazol-2-ylamide (55 mg, 0.17 mmol) in tetrahydrofuran (0.5 mL) at 25° C. was treated with formic acid (0.03 mL). The reaction solution was cooled to 0° C. and then treated with a 30% aqueous hydrogen peroxide solution (94 mg, 0.83 mmol). The reaction was stirred at 0° C. for 15 min and then was allowed to warm to 25° C. where it was stirred for 2 h. At this time, the reaction was re-cooled to 0° C., quenched by the addition of a saturated aqueous sodium sulfite solution, and then extracted with ethyl acetate (1×50 mL). The organic layer was washed with water (1×50 mL) and a saturated aqueous sodium chloride solution (1×50 mL), dried over magnesium sulfate, filtered, and concentrated in vacuo. The residue was treated with a solution of 3/1 ethyl acetate/hexanes. The resulting precipitate was collected by filtration and dried in vacuo to afford 1-isopropyl-6-methanesulfonyl-1H-indole-3-carboxylic acid thiazol-2-ylamide (33 mg, 55%) as a white solid: mp 247–249° C.; (ES)+-HRMS m/e calcd for $C_{16}H_{17}N_3O_3S_2$ (M+H)+ 364.0784, found 364.0788.

EXAMPLE 8

6-Fluoro-1-isopropyl-1H-indole-3-carboxylic acid thiazol-2-ylamide

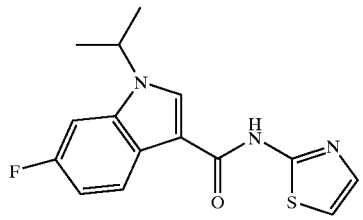

A solution of 6-fluoro-1H-indole (1.0 g, 7.40 mmol) in tetrahydrofuran (5 mL) cooled to 0° C. was treated with trifluoroacetic anhydride (1.57 mL, 11.10 mmol). The reaction was stirred at 0° C. for 1 h and then was allowed to warm to 25° C. where it was stirred for 2 h. At this time, the resulting precipitate was collected by filtration, washed with water, and dried in vacuo to afford 2,2,2-trifluoro-1-(6-fluoro-1H-indol-3-yl)-ethanone (330 mg, 19.3%) as a white solid: mp 234–235° C.; EI-HRMS m/e calcd for $C_{10}H_5F_4NO$ (M+) 231.0307, found 231.0307.

A solution of 2,2,2-trifluoro-1-(6-fluoro-1H-indol-3-yl)-ethanone (1.63 g, 7.05 mmol) in N,N-dimethylformamide (15 mL) at 25° C. was treated with potassium carbonate (2.44 g, 17.63 mmol). The resulting mixture was stirred at 25° C. for 15 min. At this time, the reaction was treated with 2-iodopropane (1.06 mL, 10.58 mmol). The reaction was heated at 65° C. for 18 h. At this time, the reaction was cooled to 25° C. and was partitioned between water (100 mL) and ethyl acetate (100 mL). The organic layer was washed with a 1N aqueous hydrochloric acid solution (1×25 mL) and a saturated aqueous sodium chloride solution (1×100 mL), dried over magnesium sulfate, filtered, and concentrated in vacuo. Biotage chromatography (FLASH 40M, Silica, 2/1 hexanes/ethyl acetate) afforded 2,2,2-trifluoro-1-(6-fluoro-1-isopropyl-1H-indol-3-yl)-ethanone (1.74 g, 90%) as a yellow solid: mp 67–69° C.; EI-HRMS m/e calcd for $C_{13}H_{11}F_4NO$ (M+) 273.0776, found 273.0780.

A solution of 2,2,2-trifluoro-1-(6-fluoro-1-isopropyl-1H-indol-3-yl)-ethanone (1.65 g, 6.04 mmol) in a 20% aqueous sodium hydroxide solution (25 mL) was heated at 110° C. for 18 h. At this time, the reaction was cooled to 25° C., partitioned between water (50 mL) and ethyl acetate (50 mL), and treated with a 1N aqueous hydrochloric acid solution (50 mL). The organic layer was washed with a saturated aqueous sodium chloride solution (1×100 mL), dried over magnesium sulfate, filtered, and concentrated in vacuo to afford 6-fluoro-1-isopropyl-1H-indole-3-carboxylic acid (1.29 g, 96%) as a yellow solid: mp 177–180° C.; EI-HRMS m/e calcd for $C_{12}H_{12}FNO_2$ (M+) 221.0852, found 221.0850.

A solution of triphenylphosphine (771 mg, 2.94 mmol) in methylene chloride (7 mL) cooled to 0° C. was treated with N-bromosuccinimide (523 mg, 2.94 mmol). The reaction was stirred at 0° C. for 15 min. At this time, the reaction was treated with 6-fluoro-1-isopropyl-1H-indole-3-carboxylic acid (500 mg, 2.26 mmol). The reaction was stirred at 0° C. for 15 min and then was allowed to warm to 25° C. where it was stirred for 15 min. The reaction was then treated with 2-aminothiazole (521 mg, 5.20 mmol) and stirred at 25° C. for 18 h. At this time, the mixture was partitioned between water (75 mL) and ethyl acetate (75 mL) and treated with a 1N aqueous hydrochloric acid solution (50 mL). The organic layer was then washed with a saturated aqueous sodium bicarbonate solution (1×50 mL), water (1×50 mL), and a saturated aqueous sodium chloride solution (1×50 mL). The organic layer was then dried over magnesium sulfate, filtered, and concentrated in vacuo. Biotage chromatography (FLASH 40M, Silica, 1/1 hexanes/ethyl acetate) afforded 6-fluoro-1-isopropyl-1H-indole-3-carboxylic acid thiazol-2-ylamide (160 mg, 23%) as pink solid: mp 203–204° C.; EI-HRMS m/e calcd for $C_{15}H_{14}FN_3OS$ (M+) 303.0842, found 303.0844.

EXAMPLE 9

6-Bromo-1-isopropyl-1H-indole-3-carboxylic acid thiazol-2-ylamide

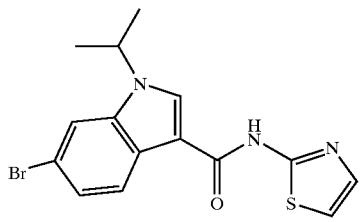

A solution of 6-bromo-1H-indole (2.0 g, 10.20 mmol) in tetrahydrofuran (10 mL) cooled to 0° C. was treated with trifluoroacetic anhydride (2.16 mL, 15.30 mmol). The reaction was stirred at 0° C. for 1 h and then was allowed to warm to 25° C. where it was stirred for 2 h. At this time, the resulting precipitate was collected by filtration, washed with water, and dried in vacuo to afford 2,2,2-trifluoro-1-(6-bromo-1H-indol-3-yl)-ethanone (1.79 g, 60%) as a white solid: mp 258–260° C.; EI-HRMS m/e calcd for $C_{10}H_5BrF_3NO$ (M+) 290.9511, found 290.9511.

A solution of 2,2,2-trifluoro-1-(6-bromo-1H-indol-3-yl)-ethanone (3.0 g, 10.27 mmol) in N,N-dimethylformamide (20 mL) at 25° C. was treated with potassium carbonate (3.54 g, 25.68 mmol). The resulting mixture was stirred at 25° C. for 15 min and then treated with 2-iodopropane (1.54 mL, 15.41 mmol). The reaction was heated at 65° C. for 18 h. At this time, the reaction was cooled to 25° C. and was partitioned between water (100 mL) and ethyl acetate (100 mL). The organic layer was then washed with a 1N aqueous hydrochloric acid solution (1×25 mL) and a saturated aqueous sodium chloride solution (1×100 mL), dried over magnesium sulfate, filtered, and concentrated in vacuo. Biotage chromatography (FLASH 40M, Silica, 2/1 hexanes/ethyl acetate) afforded 2,2,2-trifluoro-1-(6-bromo-1-isopropyl-1H-indol-3-yl)-ethanone (3.38 g, 99%) as a pink solid: mp 77–79° C.; EI-HRMS m/e calcd for $C_{13}H_{11}BrF_3NO$ (M) 332.9976, found 332.9975.

A solution of 2,2,2-trifluoro-1-(6-bromo-1-isopropyl-1H-indol-3-yl)-ethanone (3.30 g, 9.88 mmol) in a 20% aqueous sodium hydroxide solution (35 mL) was heated at 110° C. for 18 h. At this time, the reaction was cooled to 25° C., partitioned between water (100 mL) and ethyl acetate (100 mL), and treated with a 1N aqueous hydrochloric acid solution (60 mL). The organic layer was then washed with a saturated aqueous sodium chloride solution (1×100 mL), dried over magnesium sulfate, filtered, and concentrated in vacuo to afford 6-bromo-1-isopropyl-1H-indole-3-carboxylic acid (2.63 g, 94%) as a yellow solid: mp 207–209° C.; EI-HRMS m/e calcd for $C_{12}H_{12}BrNO_2$ (M+) 281.0051, found 281.0047.

A solution of triphenylphosphine (2.42 mg, 9.22 mmol) in methylene chloride (25 mL) cooled to 0° C. was treated with N-bromosuccinimide (1.64 mg, 9.22 mmol). The reaction was stirred at 0° C. for 15 min. At this time, the reaction was treated with 6-bromo-1-isopropyl-1H-indole-3-carboxylic acid (2.0 g, 7.09 mmol). The reaction was stirred at 0° C. for 15 min and then was allowed to warm to 25° C. where it was stirred for 15 min. The reaction was then treated with 2-aminothiazole (1.63 g, 16.31 mmol) and stirred at 25° C. for 18 h. At this time, the mixture was partitioned between water (150 mL) and ethyl acetate (150 mL) and treated with a 1N aqueous hydrochloric acid solution (100 mL). The organic layer was washed with a saturated aqueous sodium bicarbonate solution (1×100 mL), water (1×100 mL), and a saturated aqueous sodium chloride solution (1×100 mL). The organic layer was then dried over magnesium sulfate, filtered, and concentrated in vacuo. Biotage chromatography (FLASH 40M, Silica, 1/1 hexanes/ethyl acetate) afforded 6-bromo-1-isopropyl-1H-indole-3-carboxylic acid thiazol-2-ylamide (300 mg, 11.6%) as white solid: mp 205–207° C.; EI-HRMS m/e calcd for $C_{15}H_{14}BrN_3OS$ (M+) 363.0041, found 363.0034.

EXAMPLE 10

6-Chloro-1-isopropyl-1H-indole-3-carboxylic acid thiazol-2-ylamide

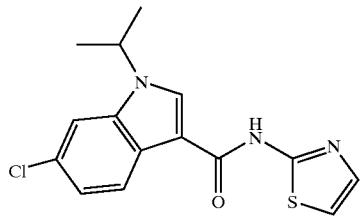

A solution of 6-chloro-1H-indole (1.0 g, 6.60 mmol) in tetrahydrofuran cooled to 0° C. was treated with trifluoroacetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_{15}ClF_3NO$ (M+) 247.0012, found 247.0006.

A solution of 1-(6-chloro-1H-indol-3-yl)-2,2,2-trifluoro-ethanone in N,N-dimethylformamide (5 mL) was treated with potassium carbonate (698 mg, 5.05 mmol). The reaction was stirred at 25° C. for 15 min and then was treated with 2-iodopropane (0.30 mL, 3.03 mmol). This mixture was heated at 65° C. for 20 h. At this time, the reaction was cooled to 25° C., quenched with water (5 mL), and then partitioned between water (50 mL) and ethyl acetate (50 mL). This mixture was treated with a saturated aqueous sodium chloride solution (1×25 mL), shaken, and separated. The organic layer was then dried over magnesium sulfate, filtered, and concentrated in vacuo. Biotage chromatography (FLASH 40M, Silica, 3/1 hexanes/ethyl acetate) afforded 1-(6-chloro-1-isopropyl-1H-indol-3-yl)-2,2,2-trifluoro-ethanone (483 mg, 83%) as a pale pink solid: mp 94–96° C.; EI-HRMS m/e calcd for $C_{13}H_{12}ClF_3NO$ (M+) 289.0481, found 289.0482.

A mixture of 1-(6-chloro-1-isopropyl-1H-indol-3-yl)-2,2,2-trifluoro-ethanone (475 mg, 1.64 mmol) in a 20% aqueous sodium hydroxide solution was heated at 110° C. for 18 h. At this time, the reaction was cooled to 25° C. and treated with a 1N aqueous hydrochloric acid solution. This solution was extracted with ethyl acetate (1×50 mL). The organic layer was dried over magnesium sulfate, filtered, and concentrated in vacuo to afford 6-chloro-1-isopropyl-1H-indole-3-carboxylic acid (385 mg, 99%) as a yellow solid: mp 206–208° C.; EI-HRMS m/e calcd for $C_{12}H_{12}ClNO_2$ (M$^+$) 237.0056, found 237.0554.

A solution of triphenylphosphine (179 mg, 0.68 mmol) in methylene chloride (3 mL) cooled to 0° C. was treated with N-bromosuccinimide (122 mg, 0.68 mmol). This solution was stirred at 0° C. for 15 min. At this time, the reaction was treated with 6-chloro-1-isopropyl-1H-indole-3-carboxylic acid (125 mg, 0.53 mmol). This solution was stirred at 0° C. for 5 min and then was allowed to warm to 25° C. where it was stirred for 30 min. The reaction was then treated with 2-amino-thiazole (121 mg, 1.21 mmol) and was stirred at 25° C. for 3 d. At this time, the reaction was partitioned between water (30 mL) and ethyl acetate (30 mL). The organic layer was separated and then washed with a 1N aqueous hydrochloric acid solution (1×20 mL), a saturated aqueous sodium bicarbonate solution (1×20 mL), water (1×20 mL), and a saturated aqueous sodium chloride solution (1×20 mL). The organic layer was then dried over magnesium sulfate, filtered, and concentrated in vacuo. Biotage chromatography (FLASH 40S, Silica, 1/1 hexanes/ethyl acetate) afforded 6-chloro-1-isopropyl-1H-indole-3-carboxylic acid thiazol-2-ylamide (62 mg, 37%) as a pink solid: mp 202–204° C.; EI-HRMS m/e calcd for $C_{17}H_{16}ClN_3O$ (M$^+$) 319.0546, found 319.0547.

EXAMPLE 11

6-Chloro-1-ethyl-1H-indole-3-carboxylic acid thiazol-2-ylamide

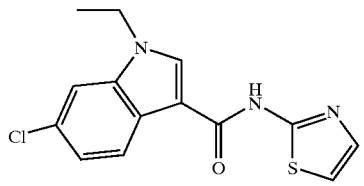

A solution of 6-chloro-1H-indole (1.0 g, 6.60 mmol) in tetrahydrofuran cooled to 0° C. was treated with trifluoroacetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_{15}ClF_3NO$ (M$^+$) 247.0012, found 247.0006.

A mixture of 1-(6-chloro-1H-indol-3-yl)-2,2,2-trifluoro-ethanone (300 mg, 1.21 mmol), potassium carbonate (419 mg, 3.03 mmol), and iodoethane (0.14 mL, 1.82 mmol) in N,N-dimethylformamide (4 mL) in a sealed reaction vessel was heated at 60° C. for 16 h. At this time, the reaction was cooled to 25° C. and partitioned between water (30 mL) and ethyl acetate (30 mL). This mixture was treated with a 1N aqueous hydrochloric acid solution (6 mL), shaken, and separated. The organic layer was concentrated in vacuo to afford a yellow solid. The resulting solid was then treated with a 20% aqueous sodium hydroxide solution (7 mL) and was heated at 115° C. for 24 h. At this time, the reaction was cooled to 25° C. and was partitioned between water (75 mL) and ethyl acetate (75 mL). This solution was treated with a 1N aqueous hydrochloric acid solution (25 mL), shaken, and separated. The organic layer was washed with a saturated aqueous sodium chloride solution (1×50 ml), dried over magnesium sulfate, filtered, and concentrated in vacuo to afford 6-chloro-1-ethyl-1H-indole-3-carboxylic acid (250 mg, 92%) as a pale yellow solid: mp 225–227° C.; EI-HRMS m/e calcd for $C_{11}H_{10}ClNO_2$ (M$^+$) 223.0400, found 223.0400.

A solution of 6-chloro-1-ethyl-1H-indole-3-carboxylic acid (240 mg, 1.07 mmol) in methylene chloride (3 mL) was cooled to 0° C. and then treated with N,N-dimethylformamide (1 drop) and oxalyl chloride (0.14 mL, 1.61 mmol). The reaction was stirred at 0° C. for 15 min and then was allowed to warm to 25° C. where it was stirred for 1 h. At this time, the reaction was concentrated in vacuo. The residue was dissolved in methylene chloride (1 mL), and this mixture was then added to a solution of 2-aminothiazole (214 mg, 2.14 mmol) and triethylamine (0.30 mL, 2.14 mmol) in N,N-dimethylformamide (2 mL). This mixture was stirred at 25° C. for 16 h. At this time, the reaction was partitioned between water (40 mL) and ethyl acetate (40 mL). This mixture was then treated with a 1N aqueous hydrochloric acid solution (15 mL). The organic layer was washed with a saturated aqueous sodium bicarbonate solution (1×30 mL), water (1×30 mL), and a saturated aqueous sodium chloride solution (1×30 mL). The organic layer was then dried over magnesium sulfate, filtered, and concentrated in vacuo. Recrystallization from ethyl acetate afforded 6-chloro-1-ethyl-1H-indole-3-carboxylic acid thiazol-2-ylamide (27 mg, 8%) as a pale yellow solid: mp 234–236° C.; EI-HRMS m/e calcd for $C_{14}H_{12}ClN_3OS$ (M$^+$) 305.0390, found 305.0383.

EXAMPLE 12

6-Chloro-1-propyl-1H-indole-3-carboxylic acid thiazol-2-ylamide

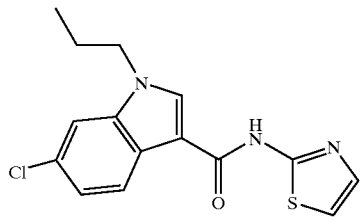

A solution of 6-chloro-1H-indole (1.0 g, 6.60 mmol) in tetrahydrofuran cooled to 0° C. was treated with trifluoroacetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_{15}CF_3NO$ (M$^+$) 247.0012, found 247.0006.

A mixture of 1-(6-chloro-1H-indol-3-yl)-2,2,2-trifluoro-ethanone (200 mg, 0.81 mmol) and potassium carbonate (214 mg, 2.02 mmol) in N,N-dimethylformamide (4 mL) was stirred at 25° C. for 30 min. At this time, the reaction was treated with 1-iodopropane (0.12 mL, 1.21 mmol) and heated at 60° C. for 5 h. The reaction mixture was cooled to 25° C. and then concentrated in vacuo. The residue was diluted with ethyl acetate (50 mL) and was washed with a saturated aqueous sodium bicarbonate solution (1×50 mL), water (2×50 mL) and a saturated aqueous sodium chloride solution (1×50 mL). The organic layer was dried over magnesium sulfate, filtered, and concentrated in vacuo to afford 1-(6-chloro-1-propyl-1H-indol-3-yl)-2,2,2-trifluoro-ethanone (277.1 mg) as an orange solid which was used without further purification or characterization.

A mixture of 1-(6-chloro-1-propyl-1H-indol-3-yl)-2,2,2-trifluoro-ethanone (277.1 mg, 0.81 mmol) in a 20% aqueous sodium hydroxide solution (2.7 mL) was heated under reflux for 17 h. At this time, the reaction was cooled to 25° C., partitioned between water (75 mL) and ethyl acetate (75 mL), and extracted with diethyl ether (1×50 mL). The aqueous layer was acidified to pH=1 with concentrated hydrochloric acid and then extracted with ethyl acetate (1×75 mL). The combined organic layers were washed with water (1×50 mL) and a saturated aqueous sodium chloride solution (1×50 mL), dried over sodium sulfate, filtered, and concentrated in vacuo to afford 6-chloro-1-propyl-1H-indole-3-carboxylic acid (141.4 mg, 74%) as a cream-colored solid: mp 179–180° C.; EI-HRMS m/e calcd for $C_{12}H_{12}ClNO_2$ (M$^+$) 237.0556, found 237.0558.

A solution of triphenylphosphine (172 mg, 0.66 mmol) in methylene chloride (2 mL) cooled to 0° C. was treated with N-bromosuccinimide (117 mg, 0.66 mmol). The reaction was stirred at 0° C. for 10 min. At this time, the reaction was treated with 6-chloro-1-propyl-1H-indole-3-carboxylic acid (120 mg, 0.50 mmol). The reaction was stirred at 0° C. for 10 min and then was allowed to warm to 25° C. where it was stirred for 30 min. The reaction was then treated with 2-aminothiazole (126 mg, 1.26 mmol) and stirred at 25° C. for 3 d. At this time, the reaction was partitioned between water (50 mL) and ethyl acetate (50 mL). This mixture was treated with a 10% aqueous hydrochloric acid solution (15 mL), shaken, and separated. The organic layer was washed with a saturated aqueous sodium bicarbonate solution (1×25 mL), water (1×25 mL), and a saturated aqueous sodium chloride solution (1×25 mL). The organic layer was then dried over magnesium sulfate, filtered, and concentrated in vacuo. Biotage chromatography (FLASH 40S, Silica, 1/1 hexanes/ethyl acetate) provided a light pink solid which was slurried with a 3/1 ethyl acetate/hexanes solution. The solid was collected by filtration to afford 6-chloro-1-propyl-1H-indole-3-carboxylic acid thiazol-2-ylamide (47 mg, 29%) as a white solid: mp 175–176° C.; EI-HRMS m/e calcd for $C_{15}H_{14}ClN_3O$ (M$^+$) 319.0546, found 319.0540.

EXAMPLE 13

1-Butyl-6-chloro-1H-indole-3-carboxylic acid thiazol-2-ylamide

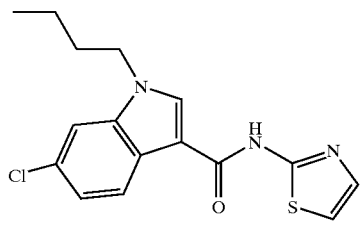

A solution of 6-chloro-1H-indole (1.0 g, 6.60 mmol) in tetrahydrofuran cooled to 0° C. was treated with trifluoro-acetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_{15}ClF_3NO$ (M$^+$) 247.0012, found 247.0006.

A mixture of 1-(6-chloro-1H-indol-3-yl)-2,2,2-trifluoro-ethanone (200 mg, 0.81 mmol) and potassium carbonate (214 mg, 2.02 mmol) in N,N-dimethylformamide (2.0 mL) was stirred at 25° C. for 30 min. The reaction was then treated with 1-iodobutane (0.14 mL, 1.21 mmol) and heated at 60° C. for 5 h. At this time, the reaction was cooled to 25° C. and concentrated in vacuo. The residue was diluted with ethyl acetate (50 mL) and was washed with a saturated aqueous sodium bicarbonate solution (1×50 mL), water (2×50 mL) and a saturated aqueous sodium chloride solution (1×50 mL). The organic layer was dried over magnesium sulfate, filtered, and concentrated in vacuo to afford 1-(1-butyl-6-chloro-1H-indol-3-yl)-2,2,2-trifluoro-ethanone (283.7 mg) as an orange oil which was used without further purification or characterization.

A mixture of 1-(1-butyl-6-chloro-1H-indol-3-yl)-2,2,2-trifluoro-ethanone (283.7 mg, 0.81 mmol) in a 20% aqueous sodium hydroxide solution (2.7 mL) was heated under reflux for 17 h. At this time, the reaction was cooled to 25° C. and was diluted with water (75 mL). This mixture was extracted with diethyl ether (1×50 mL). The aqueous layer was acidified to pH=1 with concentrated hydrochloric acid and then extracted with ethyl acetate (1×75 mL). The combined organic layers were washed with water (1×50 mL) and a saturated aqueous sodium chloride solution (1×50 mL), dried over sodium sulfate, filtered, and concentrated in vacuo to afford 1-butyl-6-chloro-1H-indole-3-carboxylic acid (141.4 mg, 69.6%) as a pale orange solid: mp 149–151° C.; EI-HRMS m/e calcd for $C_{13}H_{14}ClNO_2$ (M$^+$) 251.0713, found 251.0721.

A solution of triphenylphosphine (176 mg, 0.67 mmol) in methylene chloride (2 mL) cooled to 0° C. was treated with N-bromosuccinimide (119 mg, 0.67 mmol). The reaction was stirred at 0° C. for 10 min. At this time, the reaction was treated with 1-butyl-6-chloro-1H-indole-3-carboxylic acid (130 mg, 0.52 mmol). The reaction was stirred at 0° C. for 10 min and then was allowed to warm to 25° C. where it was stirred for 30 min. The reaction was then treated with 2-aminothiazole (129 mg, 1.29 mmol) and stirred at 25° C. for 3 d. At this time, the reaction was partitioned between water (50 mL) and ethyl acetate (50 mL). This mixture was treated with a 10% aqueous hydrochloric acid solution (15 mL), shaken, and separated. The organic layer was washed with a saturated aqueous sodium bicarbonate solution (1×25 mL), water (1×25 mL), and a saturated aqueous sodium chloride solution (1×25 mL). The organic layer was then dried over magnesium sulfate, filtered, and concentrated in vacuo. Biotage chromatography (FLASH 40S, Silica, 1/1 hexanes/ethyl acetate) provided a light, pink solid which was slurried with a 3/1 ethyl acetate/hexanes solution. The solid was collected by filtration to afford 1-butyl-6-chloro-1H-indole-3-carboxylic acid thiazol-2-ylamide (45 mg, 26%) as a white solid: mp 168–169° C.; EI-HRMS m/e calcd for $C_{16}H_{16}ClN_3OS$ (M$^+$) 333.0702, found 333.0699.

EXAMPLE 14

6-Chloro-1-isobutyl-1H-indole-3-carboxylic acid thiazol-2-ylamide

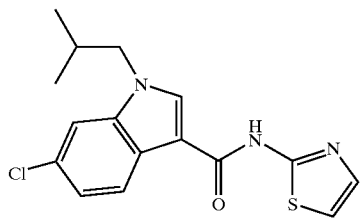

A solution of 6-chloro-1H-indole (1.0 g, 6.60 mmol) in tetrahydrofuran cooled to 0° C. was treated with trifluoroacetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_{15}ClF_3NO$ (M$^+$) 247.0012, found 247.0006.

A mixture of 1-(6-chloro-1H-indol-3-yl)-2,2,2-trifluoro-ethanone (200 mg, 0.81 mmol) and potassium carbonate (214 mg, 2.02 mmol) in N,N-dimethylformamide (2 mL) was stirred at 25° C. for 30 min. This mixture was then treated with 1-bromo-2-methylpropane (0.13 mL, 1.21 mmol) and heated at 60° C. for 5 h. At this time, the reaction was cooled to 25° C. and concentrated in vacuo. The residue was diluted with ethyl acetate (50 mL) and was washed with a saturated aqueous sodium bicarbonate solution (1×50 mL), water (2×50 mL) and a saturated aqueous sodium chloride solution (1×50 mL). The organic layer was dried over sodium sulfate, filtered, and concentrated in vacuo to afford 1-(6-chloro-1-isobutyl-1H-indol-3-yl)-2,2,2-trifluoro-ethanone (282.7 mg) as dark yellow solid which was used without further purification or characterization.

A mixture of 1-(6-chloro-1-isobutyl-1H-indol-3-yl)-2,2,2-trifluoro-ethanone (282.7 mg, 0.81 mmol) in a 20% aqueous sodium hydroxide solution (2.7 mL) was heated under reflux for 17 h. At this time, the reaction was cooled to 25° C. and was diluted with water (75 mL). This mixture was extracted with diethyl ether (1×50 mL). The aqueous layer was acidified to pH=1 with concentrated hydrochloric acid and then extracted with ethyl acetate (1×75 mL). The combined organic layers were washed with water (1×50 mL) and a saturated aqueous sodium chloride solution (1×50 mL), dried over sodium sulfate, filtered, and concentrated in vacuo to afford 6-chloro-1-isobutyl-1H-indole-3-carboxylic acid (161.4 mg, 79%) as a cream-colored solid: mp 205–206° C.; EI-HRMS m/e calcd for $C_{13}H_{14}ClNO_2$ (M$^+$) 251.0713, found 251.0713.

A solution of triphenylphosphine (196 mg, 0.75 mmol) in methylene chloride (2 mL) cooled to 0° C. was treated with N-bromosuccinimide (133 mg, 0.75 mmol). The reaction was stirred at 0° C. for 10 min. At this time, the reaction was treated with 6-chloro-1-isobutyl-1H-indole-3-carboxylic acid (145 mg, 0.58 mmol). The reaction was stirred at 0° C. for 10 min and then was allowed to warm to 25° C. where it was stirred for 30 min. The reaction was then treated with 2-aminothiazole (144 mg, 1.44 mmol) and stirred at 25° C. for 3 d. At this time, the reaction was partitioned between water (50 mL) and ethyl acetate (50 mL). This mixture was treated with a 10% aqueous hydrochloric acid solution (15 mL), shaken, and separated. The organic layer was washed with a saturated aqueous sodium bicarbonate solution (1×25 mL), water (1×25 mL), and a saturated aqueous sodium chloride solution (1×25 mL). The organic layer was then dried over magnesium sulfate, filtered, and concentrated in vacuo. Biotage chromatography (FLASH 40S, Silica, 1/1 hexanes/ethyl acetate) provided a pink solid which was slurried with a 3/1 ethyl acetate/hexanes solution (3.0 mL). The solid was collected by filtration to afford 6-chloro-1-isobutyl-1H-indole-3-carboxylic acid thiazol-2-ylamide (57 mg, 29%) as a light pink solid: mp 200–202° C.; EI-HRMS m/e calcd for $C_{16}H_{16}ClN_3OS$ (M$^+$) 333.0702, found 333.0707.

EXAMPLE 15

6-Chloro-1-pentyl-1H-indole-3-carboxylic acid thiazol-2-ylamide

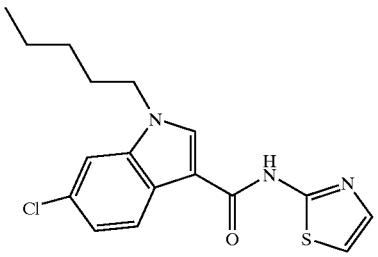

A solution of 6-chloro-1H-indole (1.0 g, 6.60 mmol) in tetrahydrofuran cooled to 0° C. was treated with trifluoroacetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_{15}ClF_3NO$ (M$^+$) 247.0012, found 247.0006.

A mixture of 1-(6-chloro-1H-indol-3-yl)-2,2,2-trifluoro-ethanone (300 mg, 1.21 mmol), potassium carbonate (419 mg, 3.03 mmol), and 1-bromopentane (0.23 mL, 1.82 mmol) in N,N-dimethylformamide (4 mL) in a sealed reaction vessel was heated at 60° C. for 16 h. At this time, the reaction was cooled to 25° C. and partitioned between water (30 mL) and ethyl acetate (30 mL). This mixture was treated with a 1N aqueous hydrochloric acid solution (6 mL), shaken, and separated. The organic layer was concentrated in vacuo to afford a yellow solid. The resulting solid was treated with a 20% aqueous sodium hydroxide solution (7 mL) and was heated at 115° C. for 24 h. At this time, the reaction was cooled to 25° C. and was partitioned between water (75 mL) and ethyl acetate (75 mL). This solution was treated with a 1N aqueous hydrochloric acid solution (25 mL), shaken, and separated. The organic layer was washed with a saturated aqueous sodium chloride solution (1×50 mL), dried over magnesium sulfate, filtered, and concentrated in vacuo to afford 6-chloro-1-pentyl-1H-indole-3-carboxylic acid (315 mg, 98%) as a yellow solid: mp 152–154° C.; EI-HRMS m/e calcd for $C_{14}H_{16}ClNO_2$ (M$^+$) 265.0870, found 265.0865.

A solution of triphenylphosphine (355 mg, 1.35 mmol) in methylene chloride (3 mL) cooled to 0° C. was treated with N-bromosuccinimide (240 mg, 1.35 mmol). The reaction was stirred at 0° C. for 15 min. At this time, the reaction was treated with 6-chloro-1-pentyl-1H-indole-3-carboxylic acid (300 mg, 1.13 mmol). The reaction was stirred at 0° C. for 10 min and then was allowed to warm to 25° C. where it was stirred for 1 h. The reaction was then treated with 2-aminothiazole (283 mg, 2.83 mmol) and stirred at 25° C. for 3 d. At this time, the reaction was partitioned between water (50 mL) and ethyl acetate (50 mL). This mixture was treated with a 10% aqueous hydrochloric acid solution (15 mL), shaken, and separated. The organic layer was washed with a saturated aqueous sodium bicarbonate solution (1×30 mL), water (1×30 mL), and a saturated aqueous sodium chloride solution (1×30 mL). The organic layer was then dried over magnesium sulfate, filtered, and concentrated in vacuo. Biotage chromatography (FLASH 40S, Silica, 2/1 hexanes/ethyl acetate) afforded 6-chloro-1-pentyl-1H-indole-3-carboxylic acid thiazol-2-ylamide (101 mg, 25%) as a pink solid: mp 139–141° C.; EI-HRMS m/e calcd for $C_{17}H_{18}ClN_3OS$ (M$^+$) 347.0859, found 347.0859.

EXAMPLE 16

6-Chloro-1-(3-methyl-butyl)-1H-indole-3-carboxylic acid thiazol-2-ylamide

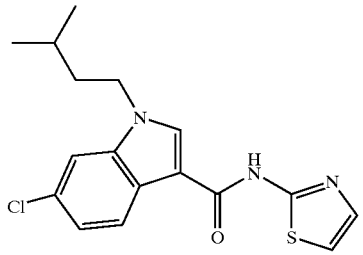

A solution of 6-chloro-1H-indole (1.0 g, 6.60 mmol) in tetrahydrofuran cooled to 0° C. was treated with trifluoroacetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_5ClF_3NO$ (M$^+$) 247.0012, found 247.0006.

A mixture of 1-(6-chloro-1H-indol-3-yl)-2,2,2-trifluoro-ethanone (200 mg, 0.81 mmol) and potassium carbonate (214 mg, 2.02 mmol) in N,N-dimethylformamide (2 mL) was stirred at 25° C. for 30 min. This mixture was then treated with 1-bromo-3-methylbutane (0.15 mL, 1.21 mmol) and then heated at 60° C. for 5 h. At this time, the reaction was cooled to 25° C. and concentrated in vacuo. The residue was diluted with ethyl acetate (50 mL) and was washed with a saturated aqueous sodium bicarbonate solution (1×50 mL), water (2×50 mL), and a saturated aqueous sodium chloride solution (1×50 mL). The organic layer was dried over sodium sulfate, filtered, and concentrated in vacuo to afford 1-[6-chloro-1-(3-methyl-butyl)-1H-indol-3-yl]-2,2,2-trifluoro-ethanone (284.9 mg) as dark yellow solid which was used without further purification or characterization.

A mixture of 1-[6-chloro-1-(3-methyl-butyl)-1H-indol-3-yl]-2,2,2-trifluoro-ethanone (284.9 mg, 0.81 mmol) in a 20% aqueous sodium hydroxide solution (2.7 mL) was heated under reflux for 17 h. At this time, the reaction was cooled to 25° C. and was diluted with water (75 mL). This mixture was extracted with diethyl ether (1×50 mL). The aqueous layer was acidified to pH=1 with concentrated hydrochloric acid and then extracted with ethyl acetate (1×75 mL). The combined organic layers were washed with water (1×50 mL) and a saturated aqueous sodium chloride solution (1×50 mL), dried over sodium sulfate, filtered, and concentrated in vacuo to afford 6-chloro-1-(3-methyl-butyl)-1H-indole-3-carboxylic acid (149.3 mg, 69.5%) as a light orange solid: mp 53–55° C.; EI-HRMS m/e calcd for $C_{14}H_{16}ClNO_2$ (M$^+$) 265.0870, found 265.0860.

A solution of triphenylphosphine (180 mg, 0.69 mmol) in methylene chloride (2 mL) cooled to 0° C. was treated with N-bromosuccinimide (122 mg, 0.69 mmol). The reaction was stirred at 0° C. for 10 min. At this time, the reaction was treated with 6-chloro-1-(3-methyl-butyl)-1H-indole-3-carboxylic acid (140 mg, 0.53 mmol). The reaction was stirred at 0° C. for 10 min and then was allowed to warm to 25° C. where it was stirred for 30 min. The reaction was then treated with 2-aminothiazole (132 mg, 1.32 mmol) and stirred at 25° C. for 3 d. At this time, the reaction was partitioned between water (50 mL) and ethyl acetate (50 mL). This mixture was treated with a 10% aqueous hydrochloric acid solution (15 mL), shaken, and separated. The organic layer was washed with a saturated aqueous sodium bicarbonate solution (1×25 mL), water (1×25 mL), and a saturated aqueous sodium chloride solution (1×25 mL). The organic layer was then dried over magnesium sulfate, filtered, and concentrated in vacuo. Biotage chromatography (FLASH 40S, Silica, 1/1 hexanes/ethyl acetate) provided a pink solid which was slurried with a 3/1 ethyl acetate/hexanes solution (3 mL). The solid was collected by filtration to afford 6-chloro-1-(3-methyl-butyl)-1H-indole-3-carboxylic acid thiazol-2-ylamide (58 mg, 31%) as a white solid: mp 179–180° C.; EI-HRMS m/e calcd for $C_{17}H_{18}ClN_3OS$ (M$^+$) 347.0859, found 347.0864.

EXAMPLE 17

6-Chloro-1-cyclopropylmethyl-1H-indole-3-carboxylic acid thiazol-2-ylamide

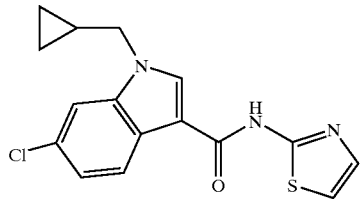

A solution of 6-chloro-1H-indole (1.0 g, 6.60 mmol) in tetrahydrofuran cooled to 0° C. was treated with trifluoroacetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_5ClF_3NO$ (M$^+$) 247.0012, found 247.0006.

A mixture of 1-(6-chloro-1H-indol-3-yl)-2,2,2-trifluoro-ethanone (300 mg, 1.21 mmol), potassium carbonate (419 mg, 3.03 mmol), and (bromomethyl)-cyclopropane (0.18 mL, 1.82 mmol) in N,N-dimethylformamide (4 mL) in a sealed reaction vessel was stirred at 60° C. for 16 h. At this time, the reaction was cooled to 25° C. and partitioned between water (30 mL) and ethyl acetate (30 mL). This mixture was treated with a 1N aqueous hydrochloric acid solution (5 mL), shaken, and separated. The organic layer was dried over magnesium sulfate, filtered, and concentrated in vacuo to afford a yellow oil. The resulting oil was treated with a 20% aqueous sodium hydroxide solution (7 mL) and was heated at 110° C. for 2 d. At this time, the reaction was cooled to 25° C. and was partitioned between water (75 mL) and ethyl acetate (75 mL). This solution was treated with a 1N aqueous hydrochloric acid solution (30 mL), shaken, and separated. The organic layer was washed with a saturated aqueous sodium chloride solution (1×50 mL), dried over magnesium sulfate, filtered, and concentrated in vacuo to afford 6-chloro-1-cyclopropylmethyl-1H-indole-3-carboxylic acid (287 mg, 95%) as a pale yellow solid: mp 219–220° C.; EI-HRMS m/e calcd for $C_{13}H_{12}ClNO_2$ ($M^+$) 249.0556, found 249.0558.

A solution of triphenylphosphine (315 mg, 1.20 mmol) in methylene chloride (3 mL) cooled to 0° C. was treated with N-bromosuccinimide (214 mg, 1.20 mmol). The reaction was stirred at 0° C. for 20 min. At this time, the reaction was treated with 6-chloro-1-cyclopropylmethyl-1H-indole-3-carboxylic acid (250 mg, 1.00 mmol). The reaction was stirred at 0° C. for 15 min and then was allowed to warm to 25° C. where it was stirred for 45 min. The reaction was then treated with 2-aminothiazole (250 mg, 2.50 mmol) and stirred at 25° C. for 24 h. At this time, the reaction was partitioned between water (50 mL) and ethyl acetate (50 mL). This mixture was treated with a 10% aqueous hydrochloric acid solution (10 mL), shaken, and separated. The organic layer was washed with a saturated aqueous sodium bicarbonate solution (1×50 mL), water (1×50 mL), and a saturated aqueous sodium chloride solution (1×50 mL), dried over magnesium sulfate, filtered, and concentrated in vacuo. Biotage chromatography (FLASH 40S, Silica, 1/1 hexanes/ethyl acetate) afforded a yellow solid. This solid was dissolved in ethyl acetate (25 mL) and was washed with a 1N aqueous sodium hydroxide solution (1×25 mL). The organic layer was dried over magnesium sulfate, filtered, and concentrated in vacuo to afford 6-chloro-1-cyclopropylmethyl-1H-indole-3-carboxylic acid thiazol-2-ylamide (25 mg, 8%) as a yellow solid: mp 185–187° C.; EI-HRMS m/e calcd for $C_{16}H_{14}ClN_3OS$ ($M^+$) 331.0542, found 331.0542.

EXAMPLE 18

6-Chloro-1-cyclobutylmethyl-1H-indole-3-carboxylic acid thiazol-2-ylamide

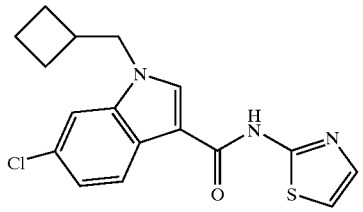

A solution of 6-chloro-1H-indole (1.0 g, 6.60 mmol) in tetrahydrofuran cooled to 0° C. was treated with trifluoroacetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_5ClF_3NO$ ($M^+$) 247.0012, found 247.0006.

A mixture of 1-(6-chloro-1H-indol-3-yl)-2,2,2-trifluoroethanone (300 mg, 1.21 mmol), potassium carbonate (419 mg, 3.03 mmol), and (bromomethyl)-cyclobutane (0.21 mL, 1.82 mmol) in N,N-dimethylformamide (4 mL) in a sealed reaction vessel was heated at 60° C. for 16 h. At this time, the reaction was cooled to 25° C. and partitioned between water (30 mL) and ethyl acetate (30 mL). This mixture was treated with a 1N aqueous hydrochloric acid solution (6 mL), shaken, and separated. The organic layer was dried over magnesium sulfate, filtered, and concentrated in vacuo to afford a yellow solid. The resulting solid was treated with a 20% aqueous sodium hydroxide solution (7 mL) and was heated at 115° C. for 24 h. At this time, the reaction was cooled to 25° C. and was partitioned between water (75 mL) and ethyl acetate (75 mL). This solution was treated with a 1N aqueous hydrochloric acid solution (30 mL), shaken, and separated. The organic layer was washed with a saturated aqueous sodium chloride solution (1×50 mL), dried over magnesium sulfate, filtered, and concentrated in vacuo to afford 6-chloro-1-cyclobutylmethyl-1H-indole-3-carboxylic acid (318 mg, 99%) as a yellow solid: mp 191–193° C.; EI-HRMS m/e calcd for $C_{14}H_{14}ClNO_2$ ($M^+$) 263.0713, found 263.0715.

A solution of triphenylphosphine (358 mg, 1.37 mmol) in methylene chloride (3 mL) cooled to 0° C. was treated with N-bromosuccinimide (243 mg, 1.37 mmol). The reaction was stirred at 0° C. for 15 min. At this time, the reaction was treated with 6-chloro-1-cyclobutylmethyl-1H-indole-3-carboxylic acid (300 mg, 1.14 mmol). The reaction was stirred at 0° C. for 10 min and then was allowed to warm to 25° C. where it was stirred for 1 h. The reaction was then treated with 2-aminothiazole (285 mg, 2.85 mmol) and stirred at 25° C. for 18 h. At this time, the reaction was partitioned between water (50 mL) and ethyl acetate (50 mL). This mixture was treated with a 10% aqueous hydrochloric acid solution (15 mL), shaken, and separated. The organic layer was washed with a saturated aqueous sodium bicarbonate solution (1×30 mL), water (1×30 mL), and a saturated aqueous sodium chloride solution (1×30 mL), dried over magnesium sulfate, filtered, and concentrated in vacuo. Biotage chromatography (FLASH 40S, Silica, 1/1 hexanes/ethyl acetate) afforded a yellow solid. This solid was dissolved in ethyl acetate (25 mL) and was washed with a 1N aqueous sodium hydroxide solution (1×25 mL). The organic layer was dried over magnesium sulfate, filtered, and concentrated in vacuo to afford 6-chloro-1-cyclobutylmethyl-1H-indole-3-carboxylic acid thiazol-2-ylamid (85 mg, 21%) as a yellow solid: mp 169–173° C.; EI-HRMS m/e calcd for $C_{17}H_{16}ClN_3OS$ ($M^+$) 345.0703, found 345.0700.

EXAMPLE 19

6-Chloro-1-cyclopentylmethyl-1H-indole-3-carboxylic acid thiazol-2-ylamide

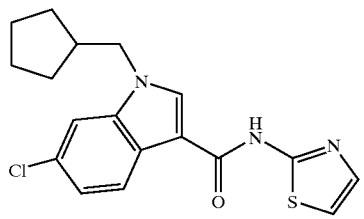

A solution of 6-chloro-1H-indole (1.0 g, 6.60 mmol) in tetrahydrofuran cooled to 0° C. was treated with trifluoroacetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_{15}ClF_3NO$ ($M^+$) 247.0012, found 247.0006.

A solution of triphenylphosphine (28.80 g, 109.8 mmol) and imidazole (14.9 g, 219.6 mmol) in methylene chloride (160 mL) was cooled to 0° C. and then slowly treated with iodine (27.87 g, 109.8 mmol). The reaction mixture was then treated dropwise with a solution of cyclopentylmethanol (10.00 g, 99.8 mmol) in methylene chloride (10 mL). The resulting reaction mixture was allowed to warm to 25° C. where it was stirred for 4 h. The reaction mixture was then diluted with water (50 mL), and the reaction mixture was further extracted with methylene chloride (3×20 mL). The combined organic layers were dried over sodium sulfate, filtered, and concentrated in vacuo at 25° C. The resulting solid was washed with pentane (4×50 mL) and filtered through a silica gel plug. The filtrate was concentrated in vacuo at 25° C. to afford iodomethylcyclopentane (18.48 g, 88%) as a clear colorless liquid: EI-HRMS m/e calcd for $C_6H_{11}I$ ($M^+$) 209.9906, found 209.9911.

A mixture of 1-(6-chloro-1H-indol-3-yl)-2,2,2-trifluoro-ethanone (300 mg, 1.21 mmol), potassium carbonate (419 mg, 3.03 mmol), and iodomethylcyclopentane (383 mg, 1.82 mmol) in N,N-dimethylformamide (4 mL) in a sealed reaction vessel was heated at 60° C. for 6 h. At this time, the reaction was cooled to 25° C. and partitioned between water (50 mL) and ethyl acetate (50 mL). This mixture was treated with a 1N aqueous hydrochloric acid solution (15 mL), shaken, and separated. The organic layer was concentrated in vacuo to afford an orange oil. The resulting oil was treated with a 20% aqueous sodium hydroxide solution (7 mL) and was heated at 110° C. for 40 h. At this time, the reaction was cooled to 25° C. and was partitioned between water (50 mL) and ethyl acetate (50 mL). This solution was treated with a 1N aqueous hydrochloric acid solution (20 mL), shaken, and separated. The organic layer was washed with a saturated aqueous sodium chloride solution (1×50 mL), dried over magnesium sulfate, filtered, and concentrated in vacuo to afford 6-chloro-1-cyclopentylmethyl-1H-indole-3-carboxylic acid (331 mg, 98%) as a yellow-orange solid: mp 181–184° C.; EI-HRMS m/e calcd for $C_{15}H_{16}ClNO_2$ ($M^+$) 277.0870, found 277.0873.

A solution of triphenylphosphine (300 mg, 1.08 mmol) in methylene chloride (3 mL) cooled to 0° C. was treated with N-bromosuccinimide (231 mg, 1.30 mmol). The reaction was stirred at 0° C. for 15 min. At this time, the reaction was treated with 6-chloro-1-cyclopentylmethyl-1H-indole-3-carboxylic acid (300 mg, 1.08 mmol). The reaction was stirred at 0° C. for 5 min and then was allowed to warm to 25° C. where it was stirred for 30 min. The reaction was then treated with 2-aminothiazole (270 mg, 2.70 mmol) and stirred at 25° C. for 20 h. At this time, the reaction was partitioned between water (30 mL) and ethyl acetate (30 mL). This mixture was treated with a 10% aqueous hydrochloric acid solution (10 mL), shaken, and separated. The organic layer was washed with a saturated aqueous sodium chloride solution (1×30 mL), dried over magnesium sulfate, filtered, and concentrated in vacuo. Biotage chromatography (FLASH 40S, Silica, 1/1 hexanes/ethyl acetate) afforded a pink foam. This foam was recrystallized from 3/1 hexanes/ethyl acetate to afford 6-chloro-1-cyclopentylmethyl-1H-indole-3-carboxylic acid thiazol-2-ylamide (87 mg, 22%) as a pink solid: mp 117–119° C.; EI-HRMS m/e calcd for $C_{18}H_{18}ClN_3OS$ ($M^+$) 359.0859, found 359.0854.

EXAMPLE 20

6-Chloro-1-cyclohexylmethyl-1H-indole-3-carboxylic acid thiazol-2-ylamide

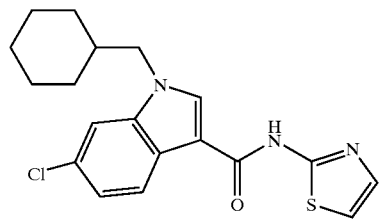

A solution of 6-chloro-1H-indole (1.0 g, 6.60 mmol) in tetrahydrofuran cooled to 0° C. was treated with trifluoro-acetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_{15}CF_3NO$ ($M^+$) 247.0012, found 247.0006.

A mixture of 1-(6-chloro-1H-indol-3-yl)-2,2,2-trifluoro-ethanone (300 mg, 1.21 mmol), potassium carbonate (419 mg, 3.03 mmol), and bromomethylcyclohexane (0.25 mL, 1.82 mmol) in N,N-dimethylformamide (4 mL) in a sealed reaction vessel was heated at 60° C. for 6 h. At this time, the reaction was cooled to 25° C. and partitioned between water (50 mL) and ethyl acetate (50 mL). This mixture was treated with a 1N aqueous hydrochloric acid solution (15 mL), shaken, and separated. The organic layer was concentrated in vacuo to afford an orange oil. The resulting oil was treated with a 20% aqueous sodium hydroxide solution (7 mL) and was heated at 110° C. for 40 h. At this time, the reaction was cooled to 25° C. and was partitioned between water (50 mL) and ethyl acetate (50 mL). This solution was treated with a 1N aqueous hydrochloric acid solution (20 mL), shaken, and separated. The organic layer was washed with a saturated aqueous sodium chloride solution (1×50 mL), dried over magnesium sulfate, filtered, and concentrated in vacuo to provide a yellow solid. The resulting solid was slurried in a solution of 3/1 hexanes/ethyl acetate for 5 min. The solid was then collected by filtration to afford 6-chloro-1-cyclohexylmethyl-1H-indole-3-carboxylic acid (247 mg, 70%) as a pale yellow solid: mp 170–172° C.; EI-HRMS m/e calcd for $C_{16}H_{18}ClNO_2$ ($M^+$) 291.1026, found 291.1026.

A solution of triphenylphosphine (240 mg, 0.82 mmol) in methylene chloride (3 mL) cooled to 0° C. was treated with N-bromosuccinimide (176 mg, 0.99 mmol). The reaction was stirred at 0° C. for 15 min. At this time, the reaction was treated with 6-chloro-1-cyclohexylmethyl-1H-indole-3-carboxylic acid (240 mg, 0.82 mmol). The reaction was stirred at 0° C. for 5 min and then was allowed to warm to 25° C. where it was stirred for 30 min. The reaction was then treated with 2-aminothiazole (206 mg, 2.06 mmol) and stirred at 25° C. for 20 h. At this time, the reaction was partitioned between water (30 mL) and ethyl acetate (30 mL). This mixture was treated with a 10% aqueous hydrochloric acid solution (10 mL), shaken, and separated. The organic layer was washed with a saturated aqueous sodium chloride solution (1×30 mL), dried over magnesium sulfate, filtered, and concentrated in vacuo. Biotage chromatography (FLASH 40S, Silica, 1/1 hexanes/ethyl acetate) afforded a pink foam. This foam was recrystallized from 3/1 hexanes/ethyl acetate to afford 6-chloro-1-cyclohexylmethyl-1H-indole-3-carboxylic acid thiazol-2-ylamide (48 mg, 16%) as a light pink solid: mp 181–183° C.; EI-HRMS m/e calcd for $C_{19}H_{20}ClN_3OS$ (M$^+$) 373.1016, found 373.1024.

EXAMPLE 21

6-Chloro-1-isopropyl-1H-indole-3-carboxylic acid [1,3,4]thiadiazol-2-ylamide

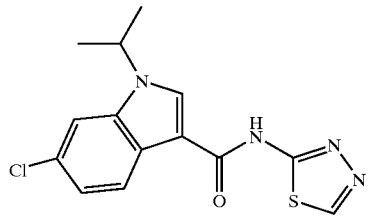

A solution of 6-chloro-1H-indole (1.0 g, 6.60 mmol) in tetrahydrofuran cooled to 0° C. was treated with trifluoroacetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_{15}ClF_3NO$ (M$^+$) 247.0012, found 247.0006.

A solution of 1-(6-chloro-1H-indol-3-yl)-2,2,2-trifluoro-ethanone in N,N-dimethylformamide (5 mL) was treated with potassium carbonate (698 mg, 5.05 mmol). The reaction was stirred at 25° C. for 15 min and then was treated with 2-iodopropane (0.30 mL, 3.03 mmol). This mixture was heated at 65° C. for 20 h. At this time, the reaction was cooled to 25° C., quenched with water (5 mL), and then partitioned between water (50 mL) and ethyl acetate (50 mL). This mixture was treated with a saturated aqueous sodium chloride solution (1×25 mL), shaken, and separated. The organic layer was then dried over magnesium sulfate, filtered, and concentrated in vacuo. Biotage chromatography (FLASH 40M, Silica, 3/1 hexanes/ethyl acetate) afforded 1-(6-chloro-1-isopropyl-1H-indol-3-yl)-2,2,2-trifluoro-ethanone (483 mg, 83%) as a pale pink solid: mp 94–96° C.; EI-HRMS m/e calcd for $C_{13}H_{11}ClF_3NO$ (M$^+$) 289.0481, found 289.0482.

A mixture of 1-(6-chloro-1-isopropyl-1H-indol-3-yl)-2,2, 2-trifluoro-ethanone (475 mg, 1.64 mmol) in a 20% aqueous sodium hydroxide solution was heated at 110° C. for 18 h. At this time, the reaction was cooled to 25° C. and treated with a 1N aqueous hydrochloric acid solution. This solution was extracted with ethyl acetate (1×50 mL). The organic layer was dried over magnesium sulfate, filtered, and concentrated in vacuo to afford 6-chloro-1-isopropyl-1H-indole-3-carboxylic acid (385 mg, 99%) as a yellow solid: mp 206–208° C.; EI-HRMS m/e calcd for $C_{12}H_{12}ClNO_2$ (M$^+$) 237.0056, found 237.0554.

A solution of 6-chloro-1-isopropyl-1H-indole-3-carboxylic acid (150 mg, 0.63 mmol) in toluene (3 mL) at 25° C. was treated with oxalyl chloride (0.09 mL, 1.10 mmol). The reaction was stirred at 25° C. for 2 h and then was treated with N,N-dimethylformamide (1 drop). The reaction was then stirred at 25° C. for 1 h. At this time, the solution was concentrated in vacuo. The residue was dissolved in toluene (2 mL) and was treated with a solution of [1,3,4]thiadiazol-2-ylamine (128 mg, 1.26 mmol) in N,N-dimethylformamide (1 mL). This mixture was stirred at 25° C. for 3 h. At this time, the reaction was partitioned between water (30 mL) and ethyl acetate (30 mL). This mixture was treated with a 1N aqueous hydrochloric acid solution (10 mL), shaken, and separated. The organic layer was washed with a saturated aqueous sodium chloride solution (1×30 mL), dried over magnesium sulfate, filtered, and concentrated in vacuo. Biotage chromatography (FLASH 40S, Silica, 1/1 hexanes/ethyl acetate) afforded a white solid. This solid was dissolved in a 1/1 hexanes/ethyl acetate solution and washed with a saturated aqueous sodium bicarbonate solution (1×10 mL) and a saturated aqueous sodium chloride solution (1×10 mL). The organic layer was dried over magnesium sulfate, filtered, and concentrated in vacuo to afford 6-chloro-1-isopropyl-1H-indole-3-carboxylic acid [1,3,4]thiadiazol-2-ylamide (12 mg, 6%) as a white solid: mp 274–275° C.; (ES)$^+$-HRMS m/e calcd for $C_{14}H_{13}ClN_4OS$ (M+H)+321.0572, found 321.0575.

EXAMPLE 22

6-Chloro-1-isopropyl-1H-indole-3-carboxylic acid (5-methyl-thiazol-2-yl)-amide

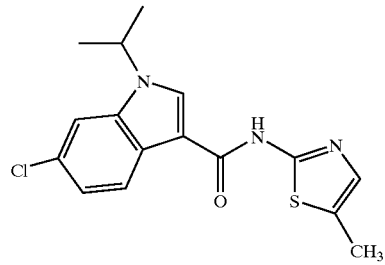

A solution of 6-chloro-1H-indole (1.0 g, 6.60 mmol) in tetrahydrofuran cooled to 0° C. was treated with trifluoroacetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_{15}ClF_3NO$ (M$^+$) 247.0012, found 247.0006.

A solution of 1-(6-chloro-1H-indol-3-yl)-2,2,2-trifluoro-ethanone in N,N-dimethylformamide (5 mL) was treated with potassium carbonate (698 mg, 5.05 mmol). The reaction was stirred at 25° C. for 15 min and then was treated with 2-iodopropane (0.30 mL, 3.03 mmol). This mixture was heated at 65° C. for 20 h. At this time, the reaction was cooled to 25° C., quenched with water (5 mL), and then partitioned between water (50 mL) and ethyl acetate (50 mL). This mixture was treated with a saturated aqueous sodium chloride solution (1×25 mL), shaken, and separated. The organic layer was then dried over magnesium sulfate, filtered, and concentrated in vacuo. Biotage chromatography (FLASH 40M, Silica, 3/1 hexanes/ethyl acetate) afforded 1-(6-chloro-1-isopropyl-1H-indol-3-yl)-2,2,2-trifluoro-ethanone (483 mg, 83%) as a pale pink solid: mp 94–96° C.; EI-HRMS m/e calcd for $C_{13}H_{11}ClF_3NO$ (M$^+$) 289.0481, found 289.0482.

A mixture of 1-(6-chloro-1-isopropyl-1H-indol-3-yl)-2,2, 2-trifluoro-ethanone (475 mg, 1.64 mmol) in a 20% aqueous sodium hydroxide solution was heated at 110° C. for 18 h.

At this time, the reaction was cooled to 25° C. and treated with a 1N aqueous hydrochloric acid solution. This solution was extracted with ethyl acetate (1×50 mL). The organic layer was dried over magnesium sulfate, filtered, and concentrated in vacuo to afford 6-chloro-1-isopropyl-1H-indole-3-carboxylic acid (385 mg, 99%) as a yellow solid: mp 206–208° C.; EI-HRMS m/e calcd for $C_{12}H_{12}ClNO_2$ ($M^+$) 237.0056, found 237.0554.

A solution of triphenylphosphine (251 mg, 0.82 mmol) in methylene chloride (3 mL) cooled to 0° C. was treated with N-bromosuccinimide (146 mg, 0.82 mmol). This solution was stirred at 0° C. for 5 min. At this time, the reaction was treated with 6-chloro-1-isopropyl-1H-indole-3-carboxylic acid (150 mg, 0.63 mmol). This solution was stirred at 0° C. for 5 min and then was allowed to warm to 25° C. where it was stirred for 30 min. The reaction was then treated with 5-methyl-thiazol-2-ylamine (166 mg, 1.45 mmol) and was stirred at 25° C. for 2 d. At this time, the reaction was diluted with water (25 mL) and ethyl acetate (25 mL). This mixture was treated with a 1N aqueous hydrochloric acid solution (5 mL). The organic layer was separated and was washed with a saturated aqueous sodium bicarbonate solution (1×10 mL) and a saturated aqueous sodium chloride solution (1×10 mL). The organic layer was dried over magnesium sulfate, filtered, and concentrated in vacuo. Biotage chromatography (FLASH 40S, Silica, 1/1 hexanes/ethyl acetate) afforded 6-chloro-1-isopropyl-1H-indole-3-carboxylic acid (5-methyl-thiazol-2-yl)-amide (120 mg, 57%) as a pink solid: mp 216–219° C.; (ES)$^+$-HRMS m/e calcd for $C_{16}H_{16}ClN_3OS$ ($M^+$) 333.0703, found 333.0708.

EXAMPLE 23

6-Chloro-1-isopropyl-1H-indole-3-carboxylic acid (4-methyl-thiazol-2-yl)-amide

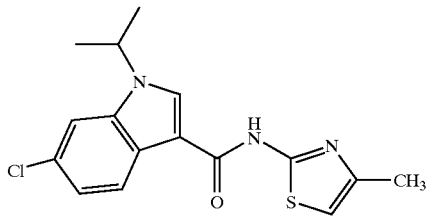

A solution of 6-chloro-1H-indole (1.0 g, 6.60 mmol) in tetrahydrofuran cooled to 0° C. was treated with trifluoro-acetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_5ClF_3NO$ ($M^+$) 247.0012, found 247.0006.

A solution of 1-(6-chloro-1H-indol-3-yl)-2,2,2-trifluoro-ethanone in N,N-dimethylformamide (5 mL) was treated with potassium carbonate (698 mg, 5.05 mmol). The reaction was stirred at 25° C. for 15 min and then was treated with 2-iodopropane (0.30 mL, 3.03 mmol). This mixture was heated at 65° C. for 20 h. At this time, the reaction was cooled to 25° C., quenched with water (5 mL), and then partitioned between water (50 mL) and ethyl acetate (50 mL). This mixture was treated with a saturated aqueous sodium chloride solution (1×25 mL), shaken, and separated. The organic layer was then dried over magnesium sulfate, filtered, and concentrated in vacuo. Biotage chromatography (FLASH 40M, Silica, 3/1 hexanes/ethyl acetate) afforded 1-(6-chloro-1-isopropyl-1H-indol-3-yl)-2,2,2-trifluoro-ethanone (483 mg, 83%) as a pale pink solid: mp 94–96° C.; EI-HRMS m/e calcd for $C_{13}H_{11}ClF_3NO$ ($M^+$) 289.0481, found 289.0482.

A mixture of 1-(6-chloro-1-isopropyl-1H-indol-3-yl)-2,2,2-trifluoro-ethanone (475 mg, 1.64 mmol) in a 20% aqueous sodium hydroxide solution was heated at 110° C. for 18 h. At this time, the reaction was cooled to 25° C. and treated with a 1N aqueous hydrochloric acid solution. This solution was extracted with ethyl acetate (1×50 mL). The organic layer was dried over magnesium sulfate, filtered, and concentrated in vacuo to afford 6-chloro-1-isopropyl-1H-indole-3-carboxylic acid (385 mg, 99%) as a yellow solid: mp 206–208° C.; EI-HRMS m/e calcd for $C_{12}H_{12}ClNO_2$ ($M^+$) 237.0056, found 237.0554.

A solution of triphenylphosphine (251 mg, 0.82 mmol) in methylene chloride (3 mL) cooled to 0° C. was treated with N-bromosuccinimide (146 mg, 0.82 mmol). This solution was stirred at 0° C. for 5 min. At this time, the reaction was treated with 6-chloro-1-isopropyl-1H-indole-3-carboxylic acid (150 mg, 0.63 mmol). This solution was stirred at 0° C. for 5 min and then was allowed to warm to 25° C. where it was stirred for 30 min. The reaction was then treated with 4-methyl-thiazol-2-ylamine (166 mg, 1.45 mmol) and was stirred at 25° C. for 2 d. At this time, the reaction was diluted with water (25 mL) and ethyl acetate (25 mL) and treated with a 1N aqueous hydrochloric acid solution (10 mL). The organic layer was separated and was washed with a saturated aqueous sodium bicarbonate solution (1×20 mL) and a saturated aqueous sodium chloride solution (1×20 mL). The organic layer was dried over magnesium sulfate, filtered, and concentrated in vacuo. Biotage chromatography (FLASH 40S, Silica, 1/1 hexanes/ethyl acetate) afforded 6-chloro-1-isopropyl-1H-indole-3-carboxylic acid (4-methyl-thiazol-2-yl)-amide (50 mg, 24%) as a yellow solid: mp 201–203° C.; (ES)$^+$-HRMS m/e calcd for $C_{16}H_{16}ClN_3OS$ ($M^+$) 333.0703, found 333.0704.

EXAMPLE 24

6-Chloro-1-isopropyl-1H-indole-3-carboxylic acid (5-chloro-thiazol-2-yl)-amide

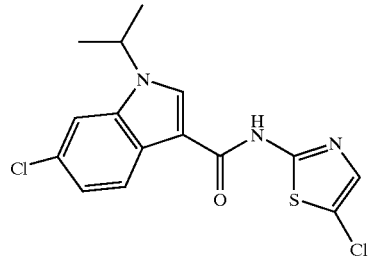

A solution of 6-chloro-1H-indole (1.0 g, 6.60 mmol) in tetrahydrofuran cooled to 0° C. was treated with trifluoro-acetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_{15}ClF_3NO$ (M$^+$) 247.0012, found 247.0006.

A solution of 1-(6-chloro-1H-indol-3-yl)-2,2,2-trifluoro-ethanone in N,N-dimethylformamide (5 mL) was treated with potassium carbonate (698 mg, 5.05 mmol). The reaction was stirred at 25° C. for 15 min and then was treated with 2-iodopropane (0.30 mL, 3.03 mmol). This mixture was heated at 65° C. for 20 h. At this time, the reaction was cooled to 25° C., quenched with water (5 mL), and then partitioned between water (50 mL) and ethyl acetate (50 mL). This mixture was treated with a saturated aqueous sodium chloride solution (1×25 mL), shaken, and separated. The organic layer was then dried over magnesium sulfate, filtered, and concentrated in vacuo. Biotage chromatography (FLASH 40M, Silica, 3/1 hexanes/ethyl acetate) afforded 1-(6-chloro-1-isopropyl-1H-indol-3-yl)-2,2,2-trifluoro-ethanone (483 mg, 83%) as a pale pink solid: mp 94–96° C.; EI-HRMS m/e calcd for $C_{13}H_{11}ClF_3NO$ (M$^+$) 289.0481, found 289.0482.

A mixture of 1-(6-chloro-1-isopropyl-1H-indol-3-yl)-2,2,2-trifluoro-ethanone (475 mg, 1.64 mmol) in a 20% aqueous sodium hydroxide solution was heated at 110° C. for 18 h. At this time, the reaction was cooled to 25° C. and treated with a 1N aqueous hydrochloric acid solution. This solution was extracted with ethyl acetate (1×50 mL). The organic layer was dried over magnesium sulfate, filtered, and concentrated in vacuo to afford 6-chloro-1-isopropyl-1H-indole-3-carboxylic acid (385 mg, 99%) as a yellow solid: mp 206–208° C.; EI-HRMS m/e calcd for $C_{12}H_{12}ClNO_2$ (M$^+$) 237.0056, found 237.0554.

A solution of triphenylphosphine (251 mg, 0.82 mmol) in methylene chloride (4 mL) cooled to 0° C. was treated with N-bromosuccinimide (146 mg, 0.82 mmol). This solution was stirred at 0° C. for 15 min. At this time, the reaction was treated with 6-chloro-1-isopropyl-1H-indole-3-carboxylic acid (150 mg, 0.63 mmol). This solution was stirred at 0° C. for 15 min and then was allowed to warm to 25° C. where it was stirred for 30 min. The reaction was then treated with 5-chloro-thiazol-2-ylamine (248 mg, 1.45 mmol) and was stirred at 25° C. for 30 min. The reaction was then treated with N,N-diisopropylethylamine (0.22 mL, 1.26 mmol) and was stirred at 25° C. for 2 d. At this time, the reaction was diluted with water (30 mL) and ethyl acetate (30 mL). This mixture was treated with a 1N aqueous hydrochloric acid solution (10 mL). The organic layer was separated and was washed with a saturated aqueous sodium bicarbonate solution (1×25 mL) and a saturated aqueous sodium chloride solution (1×25 mL). The organic layer was dried over magnesium sulfate, filtered, and concentrated in vacuo. Biotage chromatography (FLASH 40S, Silica, 1/1 hexanes/ethyl acetate) afforded 6-chloro-1-isopropyl-1H-indole-3-carboxylic acid (5-chloro-thiazol-2-yl)-amide (30 mg, 13%) as a pink solid: mp 252–253° C.; (ES)$^+$-HRMS m/e calcd for $C_{15}H_{13}Cl_2N_3OS$ (M+H)$^+$ 354.0229, found 354.0233.

EXAMPLE 25

6-Chloro-1-isopropyl-1H-indole-3-carboxylic acid (5-bromo-thiazol-2-yl)-amide

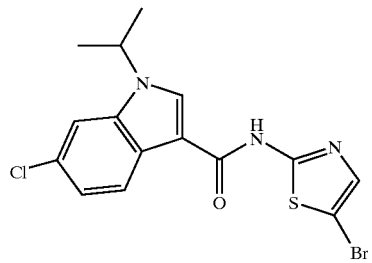

A solution of 6-chloro-1H-indole (1.0 g, 6.60 mmol) in tetrahydrofuran cooled to 0° C. was treated with trifluoro-acetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_{15}ClF_3NO$ (M$^+$) 247.0012, found 247.0006.

A solution of 1-(6-chloro-1H-indol-3-yl)-2,2,2-trifluoro-ethanone in N,N-dimethylformamide (5 mL) was treated with potassium carbonate (698 mg, 5.05 mmol). The reaction was stirred at 25° C. for 15 min and then was treated with 2-iodopropane (0.30 mL, 3.03 mmol). This mixture was heated at 65° C. for 20 h. At this time, the reaction was cooled to 25° C., quenched with water (5 mL), and then partitioned between water (50 mL) and ethyl acetate (50 mL). This mixture was treated with a saturated aqueous sodium chloride solution (1×25 mL), shaken, and separated. The organic layer was then dried over magnesium sulfate, filtered, and concentrated in vacuo. Biotage chromatography (FLASH 40M, Silica, 3/1 hexanes/ethyl acetate) afforded 1-(6-chloro-1-isopropyl-1H-indol-3-yl)-2,2,2-trifluoro-ethanone (483 mg, 83%) as a pale pink solid: mp 94–96° C.; EI-HRMS m/e calcd for $C_{13}H_{11}ClF_3NO$ (M$^+$) 289.0481, found 289.0482.

A mixture of 1-(6-chloro-1-isopropyl-1H-indol-3-yl)-2,2,2-trifluoro-ethanone (475 mg, 1.64 mmol) in a 20% aqueous sodium hydroxide solution was heated at 110° C. for 18 h. At this time, the reaction was cooled to 25° C. and treated with a 1N aqueous hydrochloric acid solution. This solution was extracted with ethyl acetate (1×50 mL). The organic layer was dried over magnesium sulfate, filtered, and concentrated in vacuo to afford 6-chloro-1-isopropyl-1H-indole-3-carboxylic acid (385 mg, 99%) as a yellow solid: mp 206–208° C.; EI-HRMS m/e calcd for $C_{12}H_{12}ClNO_2$ (M$^+$) 237.0056, found 237.0554.

A solution of triphenylphosphine (251 mg, 0.82 mmol) in methylene chloride (4 mL) cooled to 0° C. was treated with N-bromosuccinimide (146 mg, 0.82 mmol). This solution was stirred at 0° C. for 15 min. At this time, the reaction was treated with 6-chloro-1-isopropyl-1H-indole-3-carboxylic acid (150 mg, 0.63 mmol). This solution was stirred at 0° C. for 15 min and then was allowed to warm to 25° C. where it was stirred for 30 min. The reaction was then treated with 5-bromo-thiazol-2-ylamine (377 mg, 1.45 mmol) and was stirred at 25° C. for 30 min. The reaction was then treated with N,N-diisopropylethylamine (0.22 mL, 1.26 mmol) and was stirred at 25° C. for 2 d. At this time, the reaction was diluted with water (30 mL) and ethyl acetate (30 mL). This mixture was treated with a 1N aqueous hydrochloric acid solution (10 mL). The organic layer was separated and was washed with a saturated aqueous sodium bicarbonate solution (1×25 mL) and a saturated aqueous sodium chloride solution (1×25 mL). The organic layer was then dried over magnesium sulfate, filtered, and concentrated in vacuo. Biotage chromatography (FLASH 40S, Silica, 1/1 hexanes/ethyl acetate) afforded 6-chloro-1-isopropyl-1H-indole-3-carboxylic acid (5-bromo-thiazol-2-yl)-amide (33 mg, 13%) as a yellow solid: mp 240–242° C.; (ES)$^+$-HRMS m/e calcd for $C_{15}H_{13}BrClN_3OS$ (M+H)$^+$ 397.9724, found 397.9730.

EXAMPLE 26

{2-[(6-Chloro-1-isopropyl-1H-indole-3-carbonyl)-amino]-thiazol-4-yl}-acetic acid ethyl ester

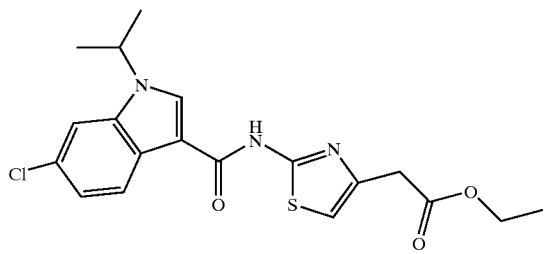

A solution of 6-chloro-1H-indole (1.0 g, 6.60 mmol) in tetrahydrofuran cooled to 0° C. was treated with trifluoroacetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_{15}ClF_3NO$ (M$^+$) 247.0012, found 247.0006.

A solution of 1-(6-chloro-1H-indol-3-yl)-2,2,2-trifluoro-ethanone in N,N-dimethylformamide (5 mL) was treated with potassium carbonate (698 mg, 5.05 mmol). The reaction was stirred at 25° C. for 15 min and then was treated with 2-iodopropane (0.30 mL, 3.03 mmol). This mixture was heated at 65° C. for 20 h. At this time, the reaction was cooled to 25° C., quenched with water (5 mL), and then partitioned between water (50 mL) and ethyl acetate (50 mL). This mixture was treated with a saturated aqueous sodium chloride solution (1×25 mL), shaken, and separated. The organic layer was then dried over magnesium sulfate, filtered, and concentrated in vacuo. Biotage chromatography (FLASH 40M, Silica, 3/1 hexanes/ethyl acetate) afforded 1-(6-chloro-1-isopropyl-1H-indol-3-yl)-2,2,2-trifluoro-ethanone (483 mg, 83%) as a pale pink solid: mp 94–96° C.; EI-HRMS m/e calcd for $C_{13}H_{11}ClF_3NO$ (M$^+$) 289.0481, found 289.0482.

A mixture of 1-(6-chloro-1-isopropyl-1H-indol-3-yl)-2,2,2-trifluoro-ethanone (475 mg, 1.64 mmol) in a 20% aqueous sodium hydroxide solution was heated at 110° C. for 18 h. At this time, the reaction was cooled to 25° C. and treated with a 1N aqueous hydrochloric acid solution. This solution was extracted with ethyl acetate (1×50 mL). The organic layer was dried over magnesium sulfate, filtered, and concentrated in vacuo to afford 6-chloro-1-isopropyl-1H-indole-3-carboxylic acid (385 mg, 99%) as a yellow solid: mp 206–208° C.; EI-HRMS m/e calcd for $C_{12}H_{12}ClNO_2$ (M$^+$) 237.0056, found 237.0554.

A solution of triphenylphosphine (182 mg, 0.69 mmol) in methylene chloride (3 mL) cooled to 0° C. was treated with N-bromosuccinimide (124 mg, 0.69 mmol). This solution was stirred at 0° C. for 15 min. At this time, the reaction was treated with 6-chloro-1-isopropyl-1H-indole-3-carboxylic acid (150 mg, 0.63 mmol). This solution was stirred at 0° C. for 5 min and then was allowed to warm to 25° C. where it was stirred for 30 min. The reaction was then treated with (2-amino-thiazol-4-yl)-acetic acid ethyl ester (294 mg, 1.58 mmol) and was stirred at 25° C. for 16 h. At this time, the reaction was diluted with water (50 mL) and ethyl acetate (50 mL). This mixture was treated with a 1N aqueous hydrochloric acid solution (10 mL). The organic layer was separated and was washed with a saturated aqueous sodium bicarbonate solution (1×25 mL) and a saturated aqueous sodium chloride solution (1×25 mL). The organic layer was dried over magnesium sulfate, filtered, and concentrated in vacuo. Biotage chromatography (FLASH 40S, Silica, 3/1 hexanes/ethyl acetate) afforded {2-[(6-chloro-1-isopropyl-1H-indole-3-carbonyl)-amino]-thiazol-4-yl}-acetic acid ethyl ester (62 mg, 24%) as an orange foam: mp 65–75° C.; (ES)$^+$-HRMS m/e calcd for $C_{19}H_{20}ClN_3O_3S$ (M+H)$^+$ 406.0987, found 406.0986.

EXAMPLE 27

6-Chloro-1-isopropyl-1H-indole-3-carboxylic acid pyridin-2-ylamide

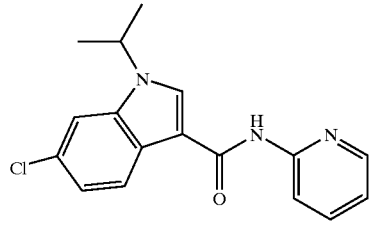

A solution of 6-chloro-1H-indole (1.0 g, 6.60 mmol) in tetrahydrofuran cooled to 0° C. was treated with trifluoroacetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_{15}ClF_3NO$ (M$^+$) 247.0012, found 247.0006.

A solution of 1-(6-chloro-1H-indol-3-yl)-2,2,2-trifluoro-ethanone in N,N-dimethylformamide (5 mL) was treated with potassium carbonate (698 mg, 5.05 mmol). The reaction was stirred at 25° C. for 15 min and then was treated with 2-iodopropane (0.30 mL, 3.03 mmol). This mixture was heated at 65° C. for 20 h. At this time, the reaction was cooled to 25° C., quenched with water (5 mL), and then partitioned between water (50 mL) and ethyl acetate (50 mL). This mixture was treated with a saturated aqueous sodium chloride solution (1×25 mL), shaken, and separated. The organic layer was then dried over magnesium sulfate, filtered, and concentrated in vacuo. Biotage chromatography (FLASH 40M, Silica, 3/1 hexanes/ethyl acetate) afforded 1-(6-chloro-1-isopropyl-1H-indol-3-yl)-2,2,2-trifluoroethanone (483 mg, 83%) as a pale pink solid: mp 94–96° C.; EI-HRMS m/e calcd for $C_{13}H_{11}ClF_3NO$ (M$^+$) 289.0481, found 289.0482.

A mixture of 1-(6-chloro-1-isopropyl-1H-indol-3-yl)-2,2,2-trifluoro-ethanone (475 mg, 1.64 mmol) in a 20% aqueous sodium hydroxide solution was heated at 110° C. for 18 h. At this time, the reaction was cooled to 25° C. and treated with a 1N aqueous hydrochloric acid solution. This solution was extracted with ethyl acetate (1×50 mL). The organic layer was dried over magnesium sulfate, filtered, and concentrated in vacuo to afford 6-chloro-1-isopropyl-1H-indole-3-carboxylic acid (385 mg, 99%) as a yellow solid: mp 206–208° C.; EI-HRMS m/e calcd for $C_{12}H_{12}ClNO_2$ (M$^+$) 237.0056, found 237.0554.

A solution of triphenylphosphine (251 mg, 0.82 mmol) in methylene chloride (3 mL) cooled to 0° C. was treated with N-bromosuccinimide (146 mg, 0.82 mmol). This solution was stirred at 0° C. for 15 min. At this time, the reaction was treated with 6-chloro-1-isopropyl-1H-indole-3-carboxylic acid (150 mg, 0.63 mmol). This solution was stirred at 0° C. for 15 min and then was allowed to warm to 25° C. where it was stirred for 30 min. The reaction was then treated with 2-amino-4,5-dimethylthiazole hydrochloride (239 mg, 1.45 mmol) and was stirred at 25° C. for 30 min. The reaction was then treated with N,N-diisopropylethylamine (0.22 mL, 1.26 mmol) and stirred at 25° C. for 2 d. At this time, the reaction was diluted with water (30 mL) and ethyl acetate (30 mL). This mixture was treated with a 1N aqueous hydrochloric acid solution (10 mL). The organic layer was separated and was washed with a saturated aqueous sodium bicarbonate solution (1×25 mL) and a saturated aqueous sodium chloride solution (1×25 mL). The organic layer was dried over magnesium sulfate, filtered, and concentrated in vacuo. Biotage chromatography (FLASH 40S, Silica, 1/1 hexanes/ethyl acetate) afforded 6-chloro-1-isopropyl-1H-indole-3-carboxylic acid pyridin-2-ylamide (483 mg, 83%) as a yellow solid: mp 149–150° C.; (ES)$^+$-HRMS m/e calcd for $C_{17}H_{16}ClN_3O$ (M+Na)$^+$ 336.0874, found 336.0876.

EXAMPLE 28

6-Chloro-1-isopropyl-1H-indole-3-carboxylic acid (5-methyl-pyridin-2-yl)-amide

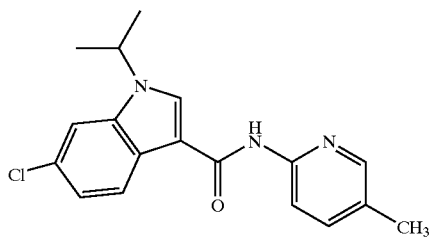

A solution of 6-chloro-1H-indole (1.0 g, 6.60 mmol) in tetrahydrofuran cooled to 0° C. was treated with trifluoroacetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_5ClF_3NO$ (M$^+$) 247.0012, found 247.0006.

A solution of 1-(6-chloro-1H-indol-3-yl)-2,2,2-trifluoro-ethanone in N,N-dimethylformamide (5 mL) was treated with potassium carbonate (698 mg, 5.05 mmol). The reaction was stirred at 25° C. for 15 min and then was treated with 2-iodopropane (0.30 mL, 3.03 mmol). This mixture was heated at 65° C. for 20 h. At this time, the reaction was cooled to 25° C., quenched with water (5 mL), and then partitioned between water (50 mL) and ethyl acetate (50 mL). This mixture was treated with a saturated aqueous sodium chloride solution (1×25 mL), shaken, and separated. The organic layer was then dried over magnesium sulfate, filtered, and concentrated in vacuo. Biotage chromatography (FLASH 40M, Silica, 3/1 hexanes/ethyl acetate) afforded 1-(6-chloro-1-isopropyl-1H-indol-3-yl)-2,2,2-trifluoro-ethanone (483 mg, 83%) as a pale pink solid: mp 94–96° C.; EI-HRMS m/e calcd for $C_{13}H_{11}ClF_3NO$ (M$^+$) 289.0481, found 289.0482.

A mixture of 1-(6-chloro-1-isopropyl-1H-indol-3-yl)-2,2,2-trifluoro-ethanone (475 mg, 1.64 mmol) in a 20% aqueous sodium hydroxide solution was heated at 110° C. for 18 h. At this time, the reaction was cooled to 25° C. and treated with a 1N aqueous hydrochloric acid solution. This solution was extracted with ethyl acetate (1×50 mL). The organic layer was dried over magnesium sulfate, filtered, and concentrated in vacuo to afford 6-chloro-1-isopropyl-1H-indole-3-carboxylic acid (385 mg, 99%) as a yellow solid: mp 206–208° C.; EI-HRMS m/e calcd for $C_{12}H_{12}ClNO_2$ (M$^+$) 237.0056, found 237.0554.

A solution of triphenylphosphine (243 mg, 0.92 mmol) in methylene chloride (3 mL) cooled to 0° C. was treated with N-bromosuccinimide (165 mg, 0.92 mmol). This solution was stirred at 0° C. for 15 min. At this time, the reaction was treated with 6-chloro-1-isopropyl-1H-indole-3-carboxylic acid (200 mg, 0.84 mmol). This solution was stirred at 0° C. for 15 min and then was allowed to warm to 25° C. where it was stirred for 30 min. The reaction was then treated with 2-amino-5-picoline (227 mg, 2.10 mmol) and was stirred at 25° C. for 18 h. At this time, the reaction was diluted with water (50 mL) and ethyl acetate (50 mL). This mixture was treated with a saturated aqueous sodium bicarbonate solution (15 mL). The organic layer was separated and was washed with a saturated aqueous sodium chloride solution (1×25 mL), dried over magnesium sulfate, filtered, and concentrated in vacuo. Biotage chromatography (FLASH 40S, Silica, 3/1 hexanes/ethyl acetate) afforded 6-chloro-1-isopropyl-1H-indole-3-carboxylic acid (5-methyl-pyridin-2-yl)-amide (53 mg, 19%) as a pale yellow solid: mp 132–134° C.; EI-HRMS m/e calcd for $C_{18}H_{18}ClN_3O$ (M$^+$) 327.1138, found 327.1135.

EXAMPLE 29

6-Chloro-1-isopropyl-1H-indole-3-carboxylic acid (5-trifluoromethyl-pyridin-2-yl)amide

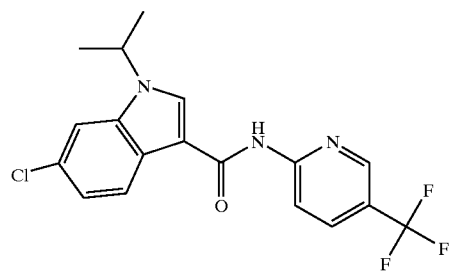

A solution of 6-chloro-1H-indole (1.0 g, 6.60 mmol) in tetrahydrofuran cooled to 0° C. was treated with trifluoroacetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_{15}ClF_3NO$ ($M^+$) 247.0012, found 247.0006.

A solution of 1-(6-chloro-1H-indol-3-yl)-2,2,2-trifluoro-ethanone in N,N-dimethylformamide (5 mL) was treated with potassium carbonate (698 mg, 5.05 mmol). The reaction was stirred at 25° C. for 15 min and then was treated with 2-iodopropane (0.30 mL, 3.03 mmol). This mixture was heated at 65° C. for 20 h. At this time, the reaction was cooled to 25° C., quenched with water (5 mL), and then partitioned between water (50 mL) and ethyl acetate (50 mL). This mixture was treated with a saturated aqueous sodium chloride solution (1×25 mL), shaken, and separated. The organic layer was then dried over magnesium sulfate, filtered, and concentrated in vacuo. Biotage chromatography (FLASH 40M, Silica, 3/1 hexanes/ethyl acetate) afforded 1-(6-chloro-1-isopropyl-1H-indol-3-yl)-2,2,2-trifluoro-ethanone (483 mg, 83%) as a pale pink solid: mp 94–96° C.; EI-HRMS m/e calcd for $C_{13}H_{11}ClF_3NO$ ($M^+$) 289.0481, found 289.0482.

A mixture of 1-(6-chloro-1-isopropyl-1H-indol-3-yl)-2,2,2-trifluoro-ethanone (475 mg, 1.64 mmol) in a 20% aqueous sodium hydroxide solution was heated at 110° C. for 18 h. At this time, the reaction was cooled to 25° C. and treated with a 1N aqueous hydrochloric acid solution. This solution was extracted with ethyl acetate (1×50 mL). The organic layer was dried over magnesium sulfate, filtered, and concentrated in vacuo to afford 6-chloro-1-isopropyl-1H-indole-3-carboxylic acid (385 mg, 99%) as a yellow solid: mp 206–208° C.; EI-HRMS m/e calcd for $C_{12}H_{12}ClNO_2$ ($M^+$) 237.0056, found 237.0554.

A solution of triphenylphosphine (243 mg, 0.92 mmol) in methylene chloride (3 mL) cooled to 0° C. was treated with N-bromosuccinimide (165 mg, 0.92 mmol). This solution was stirred at 0° C. for 15 min. At this time, the reaction was treated with 6-chloro-1-isopropyl-1H-indole-3-carboxylic acid (200 mg, 0.84 mmol). This solution was stirred at 0° C. for 15 min and then was allowed to warm to 25° C. where it was stirred for 30 min. The reaction was then treated with 2-amino-5-(trifluoromethyl)pyridine (340 mg, 2.10 mmol) and was stirred at 25° C. for 18 h. At this time, the reaction was diluted with water (50 mL) and ethyl acetate (50 mL). This mixture was treated with a saturated aqueous sodium bicarbonate solution (15 mL). The organic layer was separated and was washed with a saturated aqueous sodium chloride solution (1×25 mL), dried over magnesium sulfate, filtered, and concentrated in vacuo. Biotage chromatography (FLASH 40S, Silica, 3/1 hexanes/ethyl acetate) afforded 6-chloro-1-isopropyl-1H-indole-3-carboxylic acid (5-trifluoromethyl-pyridin-2-yl)-amide (53 mg, 19%) as a pale yellow solid: mp 179–181° C.; EI-HRMS m/e calcd for $C_{18}H_{15}ClF_3N_3O$ ($M^+$) 381.0856, found 381.0851.

EXAMPLE 30

6-Chloro-1-isopropyl-1H-indole-3-carboxylic acid (5-chloro-pyridin-2-yl)-amide

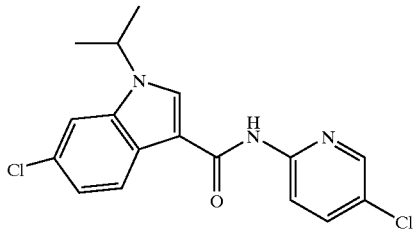

A solution of 6-chloro-1H-indole (1.0 g, 6.60 mmol) in tetrahydrofuran cooled to 0° C. was treated with trifluoro-acetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_{15}ClF_3NO$ ($M^+$) 247.0012, found 247.0006.

A solution of 1-(6-chloro-1H-indol-3-yl)-2,2,2-trifluoro-ethanone in N,N-dimethylformamide (5 mL) was treated with potassium carbonate (698 mg, 5.05 mmol). The reaction was stirred at 25° C. for 15 min and then was treated with 2-iodopropane (0.30 mL, 3.03 mmol). This mixture was heated at 65° C. for 20 h. At this time, the reaction was cooled to 25° C., quenched with water (5 mL), and then partitioned between water (50 mL) and ethyl acetate (50 mL). This mixture was treated with a saturated aqueous sodium chloride solution (1×25 mL), shaken, and separated. The organic layer was then dried over magnesium sulfate, filtered, and concentrated in vacuo. Biotage chromatography (FLASH 40M, Silica, 3/1 hexanes/ethyl acetate) afforded 1-(6-chloro-1-isopropyl-1H-indol-3-yl)-2,2,2-trifluoro-ethanone (483 mg, 83%) as a pale pink solid: mp 94–96° C.; EI-HRMS m/e calcd for $C_{13}H$, $ClF_3NO$ ($M^+$) 289.0481, found 289.0482.

A mixture of 1-(6-chloro-1-isopropyl-1H-indol-3-yl)-2,2,2-trifluoro-ethanone (475 mg, 1.64 mmol) in a 20% aqueous sodium hydroxide solution was heated at 110° C. for 18 h. At this time, the reaction was cooled to 25° C. and treated with a 1N aqueous hydrochloric acid solution. This solution was extracted with ethyl acetate (1×50 mL). The organic layer was dried over magnesium sulfate, filtered, and concentrated in vacuo to afford 6-chloro-1-isopropyl-1H-indole-3-carboxylic acid (385 mg, 99%) as a yellow solid: mp 206–208° C.; EI-HRMS m/e calcd for $C_{12}H_{12}ClNO_2$ ($M^+$) 237.0056, found 237.0554.

A solution of triphenylphosphine (243 mg, 0.92 mmol) in methylene chloride (3 mL) cooled to 0° C. was treated with N-bromosuccinimide (165 mg, 0.92 mmol). This solution was stirred at 0° C. for 15 min. At this time, the reaction was treated with 6-chloro-1-isopropyl-1H-indole-3-carboxylic acid (200 mg, 0.84 mmol). This solution was stirred at 0° C. for 15 min and then was allowed to warm to 25° C. where it was stirred for 30 min. The reaction was then treated with 2-amino-5-chloropyridine (270 mg, 2.10 mmol) and was then stirred at 25° C. for 40 h. At this time, the reaction was diluted with water (25 mL) and ethyl acetate (25 mL). This mixture was treated with a saturated aqueous sodium bicarbonate solution (10 mL). The organic layer was separated and was washed with a saturated aqueous sodium chloride solution (1×25 mL), dried over magnesium sulfate, filtered, and concentrated in vacuo. Biotage chromatography (FLASH 40S, Silica, 5/1 hexanes/ethyl acetate) afforded 6-chloro-1-isopropyl-1H-indole-3-carboxylic acid (5-chloro-pyridin-2-yl)-amide (84 mg, 29%) as a pale yellow solid: mp 131–134° C.; EI-HRMS m/e calcd for $C_{17}H_{15}Cl_2N_3O$ ($M^+$) 347.0592, found 347.0594.

EXAMPLE 31

6-Chloro-1-isopropyl-1H-indole-3-carboxylic acid (5-bromo-pyridin-2-yl)-amide

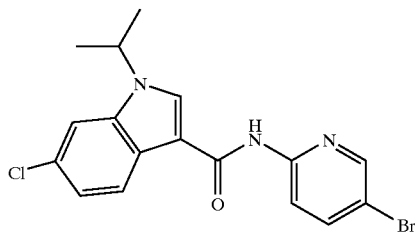

A solution of 6-chloro-1H-indole (1.0 g, 6.60 mmol) in tetrahydrofuran cooled to 0° C. was treated with trifluoroacetic anhydride. This solution was stirred at 0° C. for 30 min and then was allowed to warm to 25° C. where it was stirred for 1 h. At this time, the reaction was poured into water (75 mL). The resulting precipitate was collected by filtration, washed with water, and dried in vacuo to afford 1-(6-chloro-1H-indol-3-yl)-2,2,2-trifluoro-ethanone (1.52 g, 93%) as an off-white solid: mp 256–258° C.; EI-HRMS m/e calcd for $C_{10}H_{15}ClF_3NO$ ($M^+$) 247.0012, found 247.0006.

A solution of 1-(6-chloro-1H-indol-3-yl)-2,2,2-trifluoroethanone in N,N-dimethylformamide (5 mL) was treated with potassium carbonate (698 mg, 5.05 mmol). The reaction was stirred at 25° C. for 15 min and then was treated with 2-iodopropane (0.30 mL, 3.03 mmol). This mixture was heated at 65° C. for 20 h. At this time, the reaction was cooled to 25° C., quenched with water (5 mL), and then partitioned between water (50 mL) and ethyl acetate (50 mL). This mixture was treated with a saturated aqueous sodium chloride solution (1×25 mL), shaken, and separated. The organic layer was then dried over magnesium sulfate, filtered, and concentrated in vacuo. Biotage chromatography (FLASH 40M, Silica, 3/1 hexanes/ethyl acetate) afforded 1-(6-chloro-1-isopropyl-1H-indol-3-yl)-2,2,2-trifluoroethanone (483 mg, 83%) as a pale pink solid: mp 94–96° C.; EI-HRMS m/e calcd for $C_{13}H_{11}ClF_3NO$ ($M^+$) 289.0481, found 289.0482.

A mixture of 1-(6-chloro-1-isopropyl-1H-indol-3-yl)-2,2,2-trifluoro-ethanone (475 mg, 1.64 mmol) in a 20% aqueous sodium hydroxide solution was heated at 110° C. for 18 h. At this time, the reaction was cooled to 25° C. and treated with a 1N aqueous hydrochloric acid solution. This solution was extracted with ethyl acetate (1×50 mL). The organic layer was dried over magnesium sulfate, filtered, and concentrated in vacuo to afford 6-chloro-1-isopropyl-1H-indole-3-carboxylic acid (385 mg, 99%) as a yellow solid: mp 206–208° C.; EI-HRMS m/e calcd for $C_{12}H_{12}ClNO_2$ ($M^+$) 237.0056, found 237.0554.

A solution of triphenylphosphine (243 mg, 0.92 mmol) in methylene chloride (3 mL) cooled to 0° C. was treated with N-bromosuccinimide (165 mg, 0.92 mmol). This solution was stirred at 0° C. for 15 min. At this time, the reaction was treated with 6-chloro-1-isopropyl-1H-indole-3-carboxylic acid (200 mg, 0.84 mmol). This solution was stirred at 0° C. for 15 min and then was allowed to warm to 25° C. where it was stirred for 30 min. The reaction was then treated with 2-amino-5-bromopyridine (363 mg, 2.10 mmol) and was stirred at 25° C. for 10 d. At this time, the reaction was diluted with water (50 mL) and ethyl acetate (50 mL). This mixture was treated with a saturated aqueous sodium bicarbonate solution (25 mL). The organic layer was separated and was washed with a saturated aqueous sodium chloride solution (1×25 mL), dried over magnesium sulfate, filtered, and concentrated in vacuo. Biotage chromatography (FLASH 40M, Silica, 3/1 hexanes/ethyl acetate) afforded 6-chloro-1-isopropyl-1H-indole-3-carboxylic acid (5-bromo-pyridin-2-yl)-amide (100 mg, 30%) as an off-white foam: mp 57–64° C.; EI-HRMS m/e calcd for $C_{17}H_{15}BrClN_3O$ ($M^+$) 391.0087, found 391.0092.

BIOLOGICAL ACTIVITY EXAMPLES

Example A

In Vitro Glucokinase Activity

Glucokinase In Vitro Assay Protocol: Glucokinase (GK) was assayed by coupling the production of glucose-6-phosphate to the generation of NADH with glucose-6-phosphate dehydrogenase (G6PDH, 0.75–1 kunits/mg; Boehringer Mannheim, Indianapolis, Ind.) from Leuconostoc mesenteroides as the coupling enzyme (Scheme 2).

Scheme 2

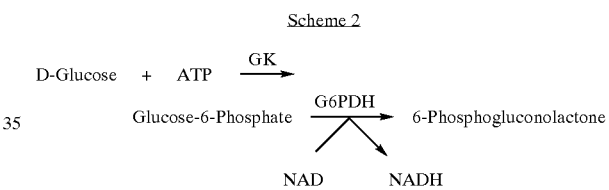

Recombinant human liver GK1 was expressed in *E. coli* as a glutathione S-transferase fusion protein (GST-GK) [Liang et al., 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al., 1995; Neet et al., 1990).

The assay was conducted at 25° C. in a flat bottom 96-well tissue culture plate from Costar (Cambridge, Mass.) with a final incubation volume of 120 μL. The incubation mixture contained the following: 25 mM Hepes buffer (pH 7.1), 25 mM KCl, 5 mM D-glucose, 1 mM ATP, 1.8 mM NAD, 2 mM $MgCl_2$, 1 μM sorbitol-6-phosphate, 1 mM dithiothreitol, test drug or 10% DMSO, 1.8 unit/ml G6PDH, and GK (see below). All organic reagents were >98% pure and were from Boehringer Mannheim with the exceptions of D-glucose and Hepes which were from Sigma Chemical Co, St Louis, Mo. Test compounds were dissolved in DMSO and were added to the incubation mixture minus GST-GK in a volume of 12 μL to yield a final DMSO concentration of 10%. This mix was pre-incubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 μL GST-GK.

After addition of enzyme, the increase in optical density (OD) at 340 nm was monitored over a 10 minute incubation period as a measure of GK activity. Sufficient GST-GK was added to produce an increase in $OD_{340}$ of 0.08 to 0.1 units over the 10 minute incubation period in wells containing 10% DMSO but no test compound. Preliminary experiments established that the GK reaction was linear over this period of time even in the presence of activators that produced a 5-fold increase in GK activity. The GK activity in control wells was compared with the activity in wells containing test GK activators. The concentration of activator that produced a 50% increase in the activity of GK was calculated and expressed as $SC_{1.5}$, the stimulatory concentration of activator required to activate the GK enzyme by 50%. All of the compounds described in the Examples had an $SC_{1.5}$ less than or equal to 100 µM.

References for Example A

Liang, Y., Kesavan, P., Wang, L., Niswender, K., Tanizawa, Y., Permut, M. A., Magnuson, M., and Matschinsky, F. M. Variable effects of maturity-onset-diabetes-of-youth (MODY)-associated glucokinase mutations on the substrate interactions and stability of the enzyme. *Biochem. J.* 309: 167–173, 1995.

Neet, K., Keenan, R. P., and Tippett, P. S. Observation of a kinetic slow transition in monomeric glucokinase. *Biochemistry* 29;770–777, 1990.

What is claimed is:

1. A compound of formula I:

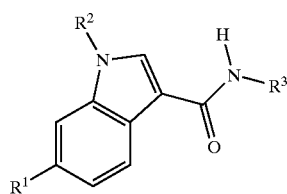

I wherein $R^1$ is halo, nitro, amino, cyano, methyl, trifluoromethyl, hydroxy, methoxy, trifluoromethoxy, methylthio, methylsulfinyl, or methylsulfonyl;

$R^2$ is lower alkyl having from 2 to 5 carbon atoms or —$CH_2$—$R^4$ wherein $R^4$ is cycloalkyl having from 3 to 6 carbon atoms; and $R^3$ is an unsubstituted or mono-substituted five- or six-membered heteroaromatic ring connected by a ring carbon atom to the amine group shown, which five- or six-membered heteroaromatic ring contains from 1 to 3 heteroatoms selected from sulfur, oxygen or nitrogen, with one heteroatom being nitrogen which is adjacent to the connecting ring carbon atom; said mono-substituted heteroaromatic ring being mono-substituted at a position on a ring carbon atom other than adjacent to said connecting carbon atom with a substituent selected from the group consisting of methyl, trifluoromethyl, chloro, bromo, nitro, cyano,

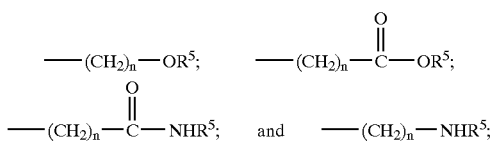

wherein n is 0 or 1;

$R^5$ is hydrogen or lower alkyl;

or a pharmaceutically acceptable salt thereof.

2. The compound according to claim 1, wherein $R^1$ is halo, nitro, methyl, trifluoromethyl, hydroxy, methoxy, methylthio, or methylsulfonyl.

3. The compound according to claim 2, wherein halo is fluoro, chloro or bromo.

4. The compound according to claim 3, wherein halo is chloro.

5. The compound according to claim 1, wherein $R^1$ is lower alkyl having from 2 to 5 carbon atoms.

6. The compound according to claim 1, wherein $R^2$ is —$CH_2$—$R^4$ wherein $R^4$ is cycloalkyl having from 3 to 6 carbon atoms.

7. The compound according to claim 6, wherein $R^4$ is cyclobutyl.

8. The compound according to claim 1, wherein $R^3$ is an unsubstituted or mono-substituted five- or six-membered heteroaromatic ring which contains from 1 to 3 heteroatoms selected from sulfur and nitrogen.

9. The compound according to claim 1, wherein said unsubstituted or mono-substituted five- or six-membered heteroaromatic ring is thiazolyl, thiadiazolyl, pyridinyl, pyrazinyl, pyridazinyl, isoxazolyl, isothiazolyl and pyrazolyl.

10. The compound according to claim 9, wherein said ring is pyridinyl or thiazolyl.

11. The compound according to claim 1, wherein said mono-substituted five- or six-membered heteroaromatic ring is substituted with methyl, trifluoromethyl, chloro, bromo, or $$\text{—}(CH_2)_n\text{—}\overset{\overset{\displaystyle O}{\|}}{C}\text{—}OR^5.$$

12. The compound according to claim 11, wherein $R^5$ is lower alkyl having 1 or 2 carbon atoms.

13. The compound according to claim 9, wherein said mono-substituted heteroaromatic ring is substituted with methyl, trifluoromethyl, chloro, bromo, or $$\text{—}(CH_2)_n\text{—}\overset{\overset{\displaystyle O}{\|}}{C}\text{—}OR^5.$$

14. The compound according to claim 9, wherein said ring is unsubstituted.

15. The compound according to claim 1, selected from the group consisting of:

1-isopropyl-6-methyl-1H-indole-3-carboxylic acid thiazol-2-ylamide;

1-isopropyl-6-trifluoromethyl-1H-indole-3-carboxylic acid thiazol-2-ylamide;

1-isopropyl-6-nitro-1H-indole-3-carboxylic acid thiazol-2-ylamide;

6-hydroxy-1-isopropyl-1H-indole-3-carboxylic acid thiazol-2-ylamide;

1-isopropyl-6-methoxy-1H-indole-3-carboxylic acid thiazol-2-ylamide;

1-isopropyl-6-methylsulfanyl-1H-indole-3-carboxylic acid thiazol-2-ylamide;

1-isopropyl-6-methanesulfonyl-1H-indole-3-carboxylic acid thiazol-2-ylamide;

6-fluoro-1-isopropyl-1H-indole-3-carboxylic acid thiazol-2-ylamide;

6-bromo-1-isopropyl-1H-indole-3-carboxylic acid thiazol-2-ylamide; and 6-chloro-1-isopropyl-1H-indole-3-carboxylic acid thiazol-2-ylamide.

16. The compound according to claim 1, selected from the group consisting of:

6-chloro-1-ethyl-1H-indole-3-carboxylic acid thiazol-2-ylamide;

6-chloro-1-propyl-1H-indole-3-carboxylic acid thiazol-2-ylamide;

1-butyl-6-chloro-1H-indole-3-carboxylic acid thiazol-2-ylamide;

6-chloro-1-isobutyl-1H-indole-3-carboxylic acid thiazol-2-ylamide;

6-chloro-1-pentyl-1H-indole-3-carboxylic acid thiazol-2-ylamide; and 6-chloro-1-(3-methyl-butyl)-1H-indole-3-carboxylic acid thiazol-2-ylamide.

17. The compound according to claim 1, selected from the group consisting of:

6-chloro-1-cyclopropylmethyl-1H-indole-3-carboxylic acid thiazol-2-ylamide;

6-chloro-1-cyclobutylmethyl-1H-indole-3-carboxylic acid thiazol-2-ylamide;

6-chloro-1-cyclopentylmethyl-1H-indole-3-carboxylic acid thiazol-2-ylamide; and 6-chloro-1-cyclohexylmethyl-1H-indole-3-carboxylic acid thiazol-2-ylamide.

18. The compound according to claim 1, selected from the group consisting of:

6-chloro-1-isopropyl-1H-indole-3-carboxylic acid [1,3,4]thiadiazol-2-ylamide; and 6-chloro-1-isopropyl-1H-indole-3-carboxylic acid pyridin-2-ylamide.

19. The compound according to claim 1, selected from the group consisting of:

6-chloro-1-isopropyl-1H-indole-3-carboxylic acid (5-methyl-thiazol-2-yl)-amide;

6-chloro-1-isopropyl-1H-indole-3-carboxylic acid (4-methyl-thiazol-2-yl)-amide;

6-chloro-1-isopropyl-1H-indole-3-carboxylic acid (5-chloro-thiazol-2-yl)-amide;

6-chloro-1-isopropyl-1H-indole-3-carboxylic acid (5-bromo-thiazol-2-yl)-amide; and {2-[(6-chloro-1-isopropyl-1H-indole-3-carbonyl)-amino]-thiazol-4-yl}-acetic acid ethyl ester.

20. The compound according to claim 1, selected from the group consisting of:

6-chloro-1-isopropyl-1H-indole-3-carboxylic acid (5-methyl-pyridin-2-yl)-amide;

6-chloro-1-isopropyl-1H-indole-3-carboxylic acid (5-trifluoromethyl-pyridin-2-yl)-amide;

6-chloro-1-isopropyl-1H-indole-3-carboxylic acid (5-chloro-pyridin-2-yl)-amide; and 6-chloro-1-isopropyl-1H-indole-3-carboxylic acid (5-bromo-pyridin-2-yl)-amide.

* * * * *

UNITED STATES PATENT AND TRADEMARK OFFICE
CERTIFICATE OF CORRECTION

PATENT NO. : 6,881,844 B2  
DATED : April 19, 2005  
INVENTOR(S) : Wendy Lea Corbett It is certified that error appears in the above-identified patent and that said Letters Patent is hereby corrected as shown below:

<u>Title page,</u>  
Item [73], Assignee, "Hoffman-La Roche Inc." should be  
-- Hoffmann-La Roche Inc. --.

<u>Column 48,</u>  
Line 10, "wherein $R^1$ is lower alkyl" should be -- wherein $R^2$ is lower alkyl --.

Signed and Sealed this

Sixteenth Day of August, 2005

JON W. DUDAS  
*Director of the United States Patent and Trademark Office*